US008609617B2

(12) United States Patent
Goldberg et al.

(10) Patent No.: US 8,609,617 B2
(45) Date of Patent: Dec. 17, 2013

(54) KLF FAMILY MEMBERS REGULATE INTRINSIC AXON REGENERATION ABILITY

(75) Inventors: Jeffrey L. Goldberg, Miami, FL (US); Vance P. Lemmon, Miami, FL (US); John Bixby, Miami, FL (US); Darcie Moore, Zurich (CH); Murray Blackmore, Miami, FL (US)

(73) Assignee: University of Miami, Miami, FL (US)

( * ) Notice: Subject to any disclaimer, the term of this patent is extended or adjusted under 35 U.S.C. 154(b) by 0 days.

(21) Appl. No.: 13/394,068

(22) PCT Filed: Sep. 7, 2010

(86) PCT No.: PCT/US2010/047982
§ 371 (c)(1),
(2), (4) Date: May 16, 2012

(87) PCT Pub. No.: WO2011/029092
PCT Pub. Date: Mar. 10, 2011

(65) Prior Publication Data
US 2012/0225084 A1    Sep. 6, 2012

Related U.S. Application Data

(60) Provisional application No. 61/239,873, filed on Sep. 4, 2009.

(51) Int. Cl.
*A61K 49/00* (2006.01)
*A61K 38/00* (2006.01)
*A61K 38/18* (2006.01)

(52) U.S. Cl.
USPC .............................. 514/17.7; 514/8.3; 424/9.1

(58) Field of Classification Search
None
See application file for complete search history.

(56) References Cited

U.S. PATENT DOCUMENTS

| 6,077,933 | A | 6/2000 | Lee et al. | |
|---|---|---|---|---|
| 6,122,122 | A | 9/2000 | Yoshida | |
| 6,841,535 | B2 | 1/2005 | Divita et al. | |
| 2005/0118606 | A1* | 6/2005 | Roth et al. | 435/6 |
| 2007/0275917 | A1 | 11/2007 | Nagai et al. | |
| 2008/0233648 | A1 | 9/2008 | Sugaya et al. | |
| 2008/0300209 | A1 | 12/2008 | Mamet | |

(Continued)

FOREIGN PATENT DOCUMENTS

WO    WO2008/008846 A2    1/2008

OTHER PUBLICATIONS

Campbell et al. (2005) Upregulation of activating transcription factor 3 (ATF3) by intrinsic CNS neurons regenerating axons into peripheral nerve grafts. Experimental neurology 192:340-347.*

(Continued)

*Primary Examiner* — Jeffrey Stucker
*Assistant Examiner* — Adam M Weidner
(74) *Attorney, Agent, or Firm* — Venable LLP; Nancy J. Axelrod; Stefan J. Kirchanski

(57) ABSTRACT

This invention relates, to a method for promoting CNS axon regeneration, comprising (1) inhibiting the expression or activity in a neuron of one or more of the members of the Krüppel-like transcription factor (KLF) family that suppress axon growth (e.g., KLF 1, 2, 3, 4, 5, 9,12, 13, 14, 15 and/or 16), and/or (2) stimulating the expression or activity in a neuron of one or more of the members of the KLF family that promote axon growth (e.g., KLF 6 and/or 7).

21 Claims, 19 Drawing Sheets

(56) References Cited

U.S. PATENT DOCUMENTS

| | | |
|---|---|---|
| 2009/0011003 A1 | 1/2009 | Yamauchi et al. |
| 2009/0098054 A1 | 4/2009 | Kufe |
| 2009/0099123 A1 | 4/2009 | Safe et al. |
| 2009/0138979 A1 | 5/2009 | Latham et al. |

OTHER PUBLICATIONS

Swamynathan et al. (2008) Identification of candidate klf4 target genes reveals the molecular basis of the diverse regulatory roles of klf4 in the mouse cornea. Invest Ophthalmol Vis Sci 49(8):3360-3370.*
Veldman et al., Gene expression analysis of zebrafish retinal ganglion cells during optic nerve regeneration identifies KLF6a and KLF7a as important regulators of axon regeneration, Dev. Bio., Dec. 15, 2007, vol. 312, No. 2, p. 596-612, the entire article, especially abstract; p. 596, col. 2, para 1; p. 598, col. 2, para 2; p. 601, col. 1, para1.
Laub et al., Transcription Factor KLF7 is important for Neuronal Morphogenesis in Selected Regions of the Nervous System Mol. Cell. Bio., Jul. 2005, vol. 25, No. 13, p. 5699-5711, the entire article, especially abstract; p. 5709, col. 1, para 1; p. 5700, col. 2, para 1-3; p. 5699, col. 1, para 1; p. 5709, col. 1 para 1.
International Search Report dated Nov. 19, 2010.
Arlotta, P., et al., "Neuronal Subtype-Specific Genes that Control Corticospinal Motor Neuron Development in Vivo", Neuron, vol. 45, 207-221, Jan. 20, 2005.
Cayrou, C., et al., "Suppression of the basic transcription element-binding protein in brain neuronal cultures inhibits thyroid hormone-induced neurite branching," Endocrinology, vol. 143, No. 6, pp. 2242-2249, 2002.
Chen, D., et al., Intrinsic Changes in Developing Retinal Neurons Result in Regenerative Failure of Their Axons, Proc. Natl. Acad. Sci., vol. 92, pp. 7287-7291, Aug. 1995.
Dang, D., et al., "Opposing Effects of Krüppel-like Factor 4 (gut-enriched Krüppel-like Factor) and Krüppel-like factor 5 (intestinal-enriched Krüppel-like Factor) on the Promoter of the Krüppel-like fctor 4 gene," Nucleic Acids Research, vol. 30, No. 13 (2002).
Eaton, S., et al., "A Network of Krüppel-like Factors (Klfs) Klf8 is Repressed by Klf3 and Activated by Klf1 In Vivo," The Journal of Biological Chemistry, vol. 283, No. 44, pp. 26937-26947 (2008).
Jiang, J., et al., "A Core Klf Circuitry Regulates Self-Renewal of Embryonic Stem Cells," Nature Cell Biology, vol. 10, No. 3 (2008).
Kaczynski, J., et al., "Sp1-and Krüppel-like Transcription Factors," Genome Biology, vol. 4, Issue 2, Art. 206 (2003).
Katz, J., "The Zinc-Finger Transcription Factor Klf4 is Required for Terminal Differentiation of Goblet Cells in the Colon," The Company of Biologists Limited, Dev. vol. 129, pp. 2619-2628 (2002).
Segre, J., "Klf4 is a Transcription Factor Required for Establishing the Barrier Function of the Skin," Nature Genetics, vol. 22 (1999).
Wang, J., et al., "Disease Gene Candidates Revealed by Expression Profiling of Retinal Ganglion Cell Development," The Journal of Neuroscience, vol. 27, Issue 32, pp. 8593-8603 (2007).
Zhang, W., et al., "Novel Cross Talk of Kruppel-Like Factor 4 and β-Catenin Regulates Normal Intestinal Homeostasis and Tumor Repression," Molecular adn Cellular Biology, vol. 26, No. 6, pp. 2005-2064 (2006).
Zhu, S., et al., "Glutamatergic Stimulation Triggers Rapid Krüpple-like Factor 4 Expression in Neurons, and the Overexpression of KLF4 Sensitizes Neurons to NMDA-induced Caspase-3 Activity," The Journal of Brain Research 1250, pp. 49-62 (2009).
Goldberg, J., et al., "Amacrine-Signaled Loss of Intrinsic Axon Growth Ability by Retinal Ganglion Cells," Science Magazine, vol. 296 (2002).
Bialkowska, A., et al., "Identification of Novel Small-Molecule Compounds That Inhibit the Proproliferative Krüppel-like Factor 5 in Colorectal Cancer Cells by High-Throughput Screening", Molecular Cancer Therapeutics, pp. 563-570, 2009.
McConnell, B., et al., "Mammalian Krüppel-Like Factors in Health and Diseases", Physiological Reviews, pp. 1337-1381, 2010.
Shen et al., "Kruppel-like Factor 4 is a Novel Mediator of Kallistatin in Inhibiting Endothelial Nitric-oxide Synthase Expression", Journal of Biological Chemistry, vol. 284, No. 51, pp. 35471-35478, (2009).
Sako et al., "Angiopoietin-1 Induces Kruppel-like Factor 2 Expression through a Phosphoinositide 3-Kinase/AKT-dependent Activation of Myocyte Enhancer Factor 2", Journal of Biological Chemistry, vol. 284, No. 9, pp. 5592-5601, (2008).
Chanchevalap et al., "Kruppel-like Factor 5 is an Important Mediator for Lipopolysaccharide-Induced Proinflammatory Response in Intenstinal Epithelial Cells", Nucleic Acids Reserch, vol. 34, No. 4. pp. 1216-1223, (2006).
PubChem BioAssay publication Luminescence-Based Dose Response Cell-Based High Throughput Screening Assay for Inhibitors of Kruppel-Like Factor 5 (KLF5).—BioAssay Summary. (1973).

* cited by examiner

Figure 8
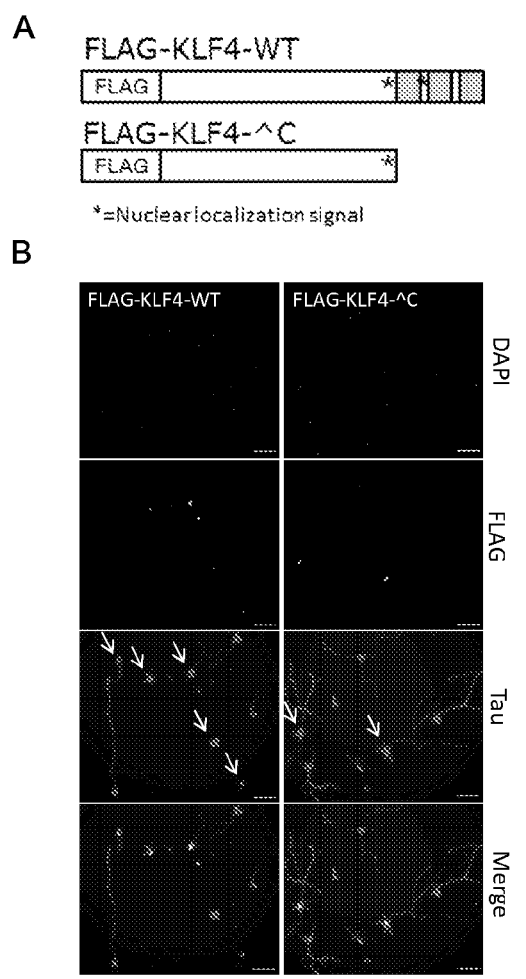
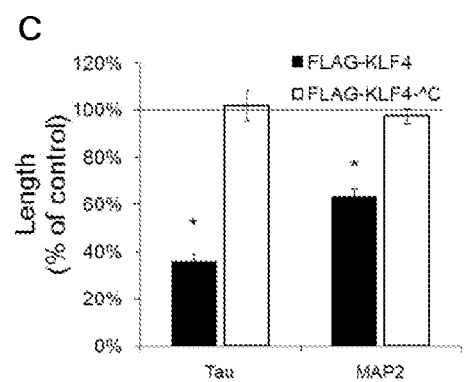

SEQUENCE LISTING

<160> NUMBER OF SEQ ID NOS: 13

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ctaggccaca gaattgaaag atct                                          24

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gtaggtggaa attctagcat catcc                                         25

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gcggtctggc agtaaaaact atc                                           23

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gtgaaacagc attgctgtca ctt                                           23

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggagcgggag aaatggatat g                                             21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aaagtcgctc tgagttgtta t                                        21

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aagaccgcga agagtttgtc                                          20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gagttcctcg gtcatttcca                                          20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tgctttcaag tgggagcttt                                          20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ttgctctctc gggacaagtt                                          20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gagctgaggg aagccttctt                                          20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aacaaatacc gacccatcca                                          20

```
<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
agactttccc acagccactg                                                    20
```

KLF FAMILY MEMBERS REGULATE INTRINSIC AXON REGENERATION ABILITY

This is a U.S. national stage application of PCT/US2010/047982, filed Sep. 7, 2010, and claims the benefit of the filing date of provisional patent application 61/239,873 filed Sep. 4, 2009, which is incorporated by reference in its entirety herein.

The research leading to this invention was supported in part by an R01 grant, number EY 016790, from the National Eye Institute (NEI); an R03 grant, number NS061348, from the National Institute of Neurological Disorders and Stroke (NINDS); a P30 grant, number EY014801, from the NEI; and NINDS training grants T32 NS07492 and T32 NS007459. The Government of the United States of America has certain rights in the invention.

SEQUENCE LISTING

The instant application contains a Sequence Listing which has been submitted in ASCII format via EFS-Web and is hereby incorporated by reference in its entirety. Said ASCII copy, created on May 15, 2012, is named 39532328.txt and is 3,353 bytes in size.

BACKGROUND INFORMATION

Adult mammalian central nervous system (CNS) axons are unable to regenerate after injury, but immature CNS neurons regenerate axons robustly. In addition to the development of an inhibitory CNS environment, a developmental loss in neurons' intrinsic capacity for axon growth is thought to contribute to regeneration failure. For example, after birth, axonal outgrowth from rat retinal ganglion cells (RGCs, a type of CNS neuron) slows substantially. Similar developmental declines in axon growth ability have been observed in mammalian tissue explants of brainstem, cerebellum, entorhinal cortex, and retina. Various cell-autonomous factors such as cAMP and CREB, Bcl-2, Rho/ROCK, Cdh1-APC, and PTEN have been suggested to play roles in this process. However, manipulating these regulators of axon growth, even when simultaneously overcoming environmental inhibition, only partially restores regeneration, suggesting that additional intrinsic axon growth regulators remain to be identified.

The inability of axons to regenerate in the central nervous system (CNS) is a major barrier to recovery from a wide range of injuries and diseases, including traumatic brain injury (e.g., traumatic optic neuropathy), stroke (including ischemic optic neuropathy), spinal cord injury, multiple sclerosis, macular degeneration, glaucoma, and other neurodegenerative diseases (e.g. Parkinson's Disease). A treatment that can stimulate CNS axon regeneration would improve outcomes for all of these afflictions, and other conditions that disrupt CNS axon tracts.

Current approaches for stimulating CNS axon regeneration in injured adult neurons generally focus on methods to improve the environment of the injured CNS. Such methods include the modulation of inflammatory responses in the spinal cord, transplantation of stem cells, and neutralizing inhibitory signaling in the CNS environment. It would be desirable to develop a new class of methods, which can boost neurons' intrinsic propensity for axon growth.

KLF4 KO RGCs have a higher percentage of cells with neurites, compared to controls (N=3; * p<0.02, t-test; mean±SEM). D) When all YFP+RGCs were measured, KLF4 KO RGCs extended longer neurites than WT RGCs (representative experiment shown; * p<0.001; mean±SEM).

Figure 5:
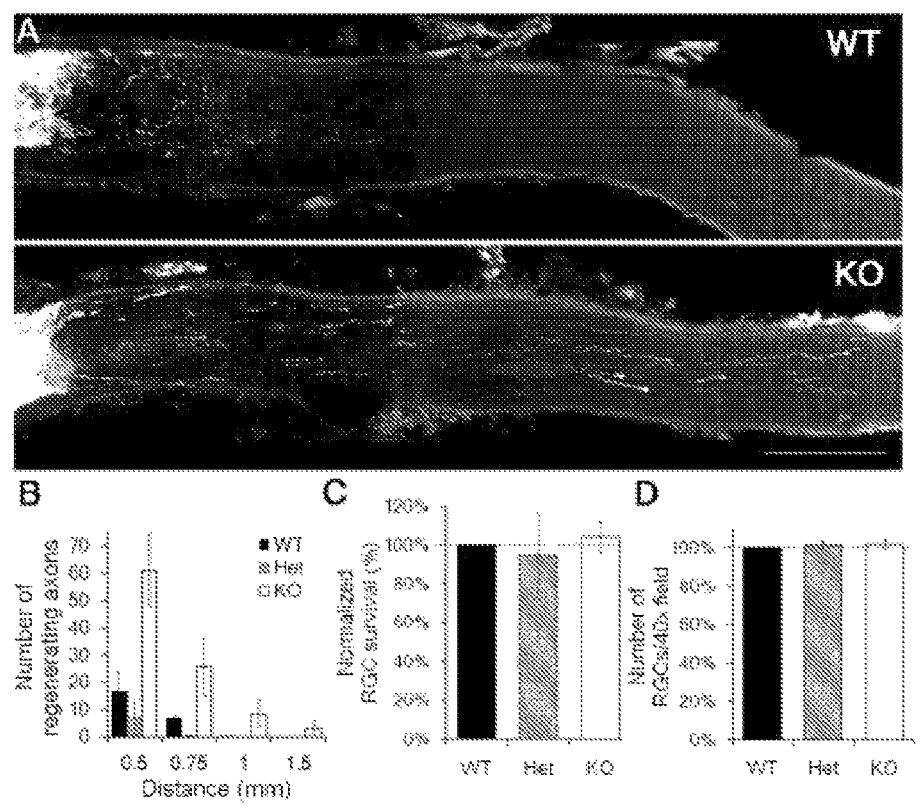

FIG. 5. KLF4 knockout during development increases regeneration of adult RGCs without altering RGC number or survival after injury. A-B) Two weeks after optic nerve crush of Thy1-cre+$^{KLF}$4+/+(WT), Thy1-cre+/KLF4$^{fl/+}$(Het), and Thy1-cre+/KLF4$^{fl/fl}$ (KO) mice, regenerating fibers were anterogradely labeled by intravitreal injection of Alexa 594-labeled cholera toxin B. Regenerating fibers were counted at specified distances from the lesion site. A) Partial projections of sectioned optic nerve from WT and KO mice show regenerating axons more than 1 mm distal to the lesion site in KO nerve. (Scale bar, 200 μm). B) More fibers regenerate in KO mice compared to WT or Het (n=10 WT, 4 Het, 7 KO; p<0.001 for KO vs WT or Het; no difference between WT and Het by mixed model analysis of covariance; mean±SEM). C-D) Retinas from these animals, normalized to WT, showed no differences in RGC survival two weeks after optic nerve crush (C; mean±SEM; n=6 WT, 4 Het, 9 KO) or in RGC number in the contralateral uninjured retinas (D; mean±SEM; n=8 WT, 4 Het, 9 KO).

Figure 6:
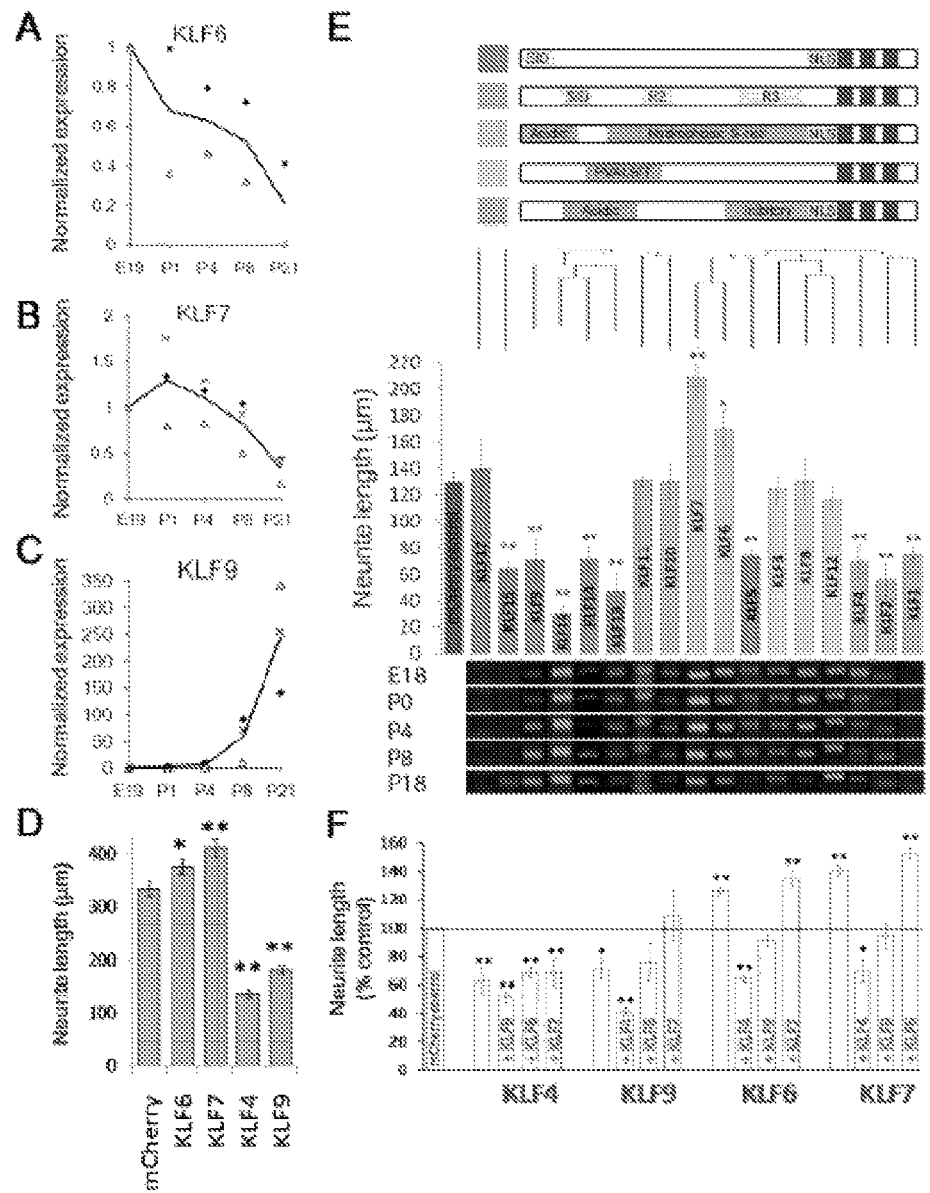

FIG. 6. Multiple KLF family members are developmentally regulated in RGCs and differentially affect CNS neurite growth. A-C) RGCs from multiple ages were purified by immunopanning and analyzed by qRT-PCR. Transcript abundance is normalized to E19. KLF6 (A) and KLF7 (B) decrease more than 5-fold postnatally, while KLF9 (C) increases-250 fold. Each marker type is a separate experiment, line is average; N=2-3. D) P4 RGCs were co-transfected with KLFs and EGFP reporter and plated for 2 days on laminin. Bars represent average total neurite length of transfected (EGFP+) neurons. (n>700; * p<0.05, ** p<0.01; ANOVA with post hoc Dunnett's test; mean±SEM; pooled data from two replicate experiments.) E) P5 cortical neurons were co-transfected with individual KLFs and mCherry, plated for 3 days on laminin, and immunostained for beta-III tubulin. (Top) KLF family members are grouped according to defined structural domains (27), and clustered by amino acid similarity (Clustal analysis, Vector NTI). (Middle) Bars represent average total neurite length of transfected (mCherry+) neurons, and are colored by the presence of known motifs (above). Nine KLFs significantly decreased neurite length, and two increased neurite length (N>3, n>100; * p<0.05, ** p<0.01, ANOVA with post hoc Dunnett's test; mean±SEM). (Bottom) Purified RGCs from different ages were analyzed by RT-PCR with KLF-specific primers, ordered according to the overlying bar graph. Transcripts for all KLFs except -1 and -17 were detected in developing RGCs. (F) P5 cortical neurons were co-transfected with combinations of KLFs with IRES-mCherry (red) or IRES-EGFP (green) reporters and cultured as above (DNA loading controls, FIG. 19). Bars represent average neurite length of dually transfected neurons (mCherry+, EGFP+). Co-expression of KLF4 or -9 blocked the growth-promoting effects of KLF6 or -7. (N=3, n>25; * p<0.05, ** p<0.01, ANOVA with post hoc Dunnett's test; mean±SEM).

Figure 7:
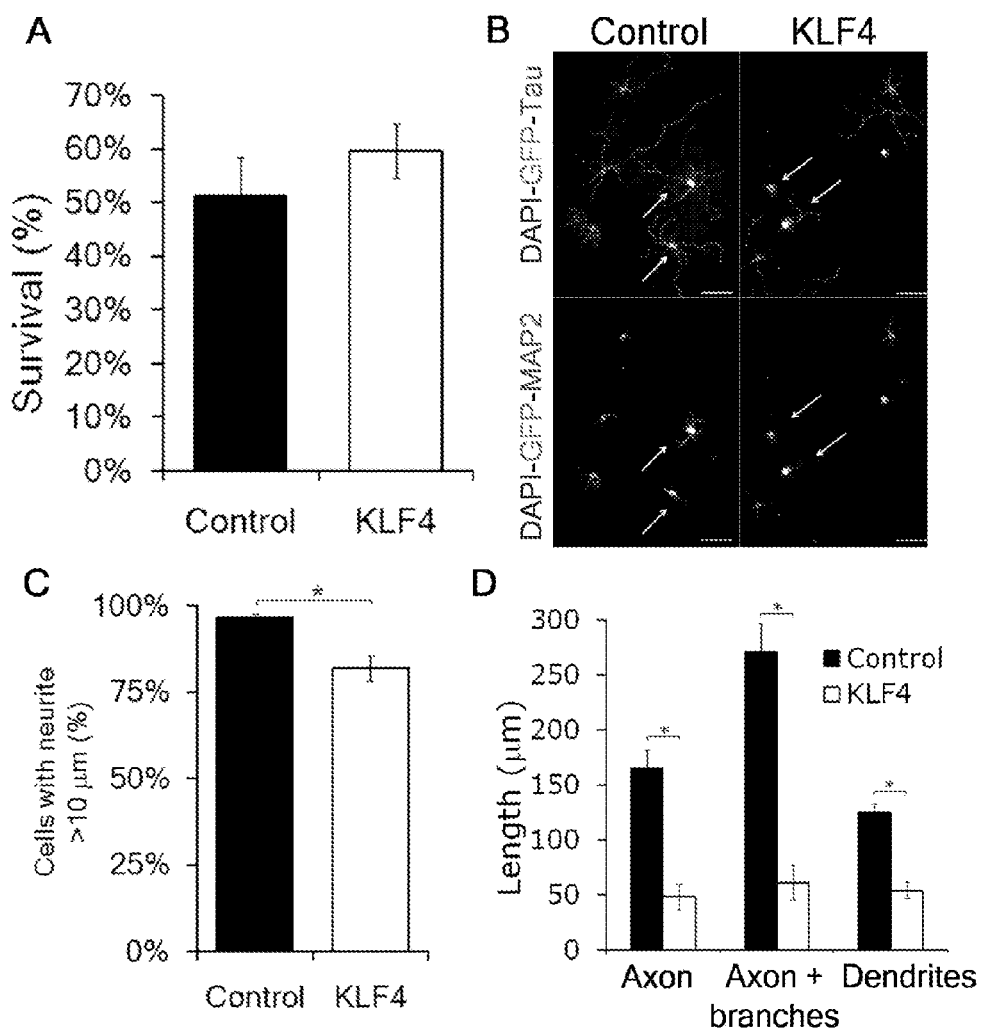

FIG. 7. KLF4 overexpression in hippocampal neurons decreases neurite growth and neurite initiation. A-D) E18 hippocampal neurons were co-transfected with KLF4 or control plus EGFP, cultured on laminin-coated plates, and immunostained for Tau (neurites) and MAP2 (dendrites). A) There was no difference in survival by nuclear morphology and DAPI intensity between control- and KLF4-transfected neurons (Mean±SD). B) Transfected EGFP+cells (arrows) were imaged to detect DAPI, EGFP, and either Tau (top) or MAP2 (bottom). KLF4-transfected neurons had shorter axons and dendrites. (Scale bar, 50μm) C) KLF4 overexpression decreased the percentage of transfected neurons that were able to extend at least 1 neurite >10 μm (N=5; * p<0.01, paired t-test; mean±SEM). D) KLF4 overexpression decreased both axon (Tau+/MAP2-) and dendrite (MAP2+) length (* p<0.01, t-test; mean±SEM).

FIG. 8. KLF4-mediated suppression of neurite growth requires the C-terminal zinc finger domain. E18 hippocampal neurons were transfected with either FLAG-KLF4-WT, FLAG-KLF4-^C, or mCherry-pIRES2-eGFP as control. A) After 3DIV, neurons were stained for Tau (neurites) and MAP2 (dendrites) prior to imaging and analysis (Cellomics KSR). Transfected neurons are indicated by arrows. B) Neurite growth was normalized to control transfected neurons (not graphed, equal to 100%). WT KLF4 overexpression significantly decreased neurite growth in both tau stained and MAP2 stained neurites, while deletion of KLF4's C-terminus led to growth indistinguishable from that of controls (* p<0.01, one representative experiment of 2 shown; mean ±SEM).

Figure 9:
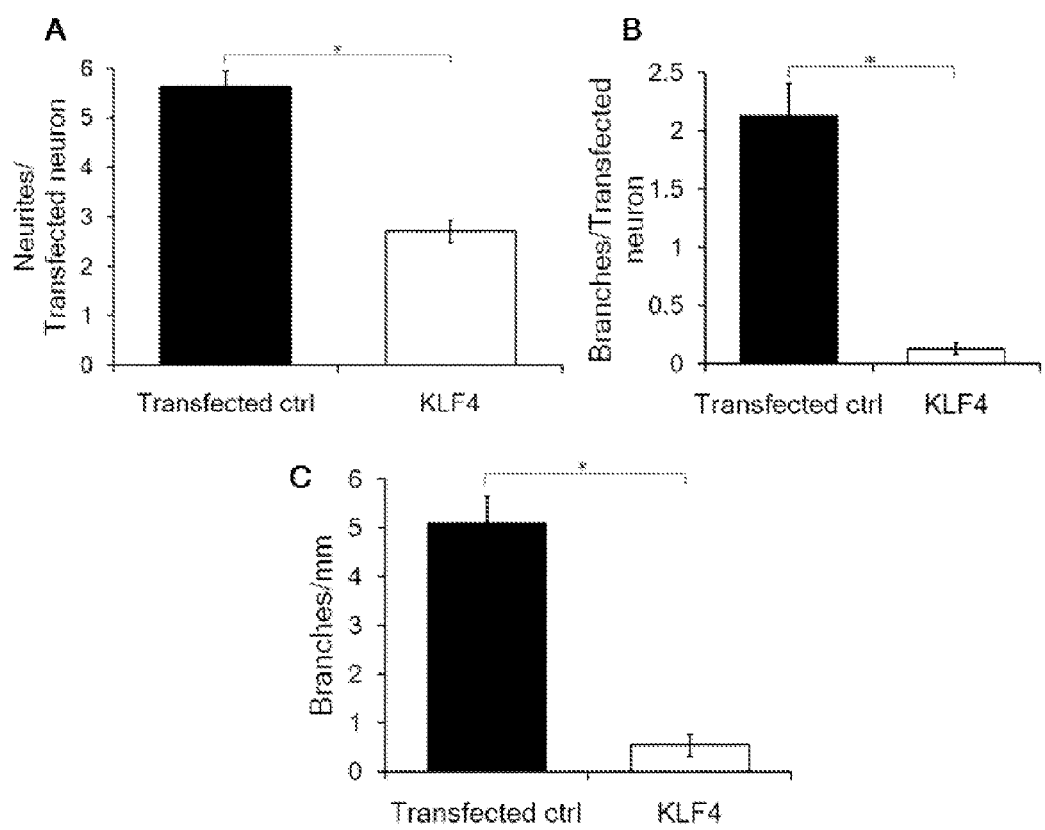

FIG. 9. KLF4 overexpression decreases numbers of both neurites and branches in embryonic hippocampal neurons. E18 hippocampal neurons were electroporated with EGFP and either KLF4 or a pcDNA3 vector control and cultured for 3 days on PDL- and laminin-coated plates in growth media. Following immunostaining, transfected neurons were imaged and hand-traced. There was a decrease in the number of neurites originating from the cell body (A), the number of branches from all neurites (B), and the number of branches normalized to the total neurite length for each transfected neuron (C) after KLF4 overexpression (*p<0.001 for each graph, unpaired t-test; n>50 per condition; mean±SEM).

Figure 10:
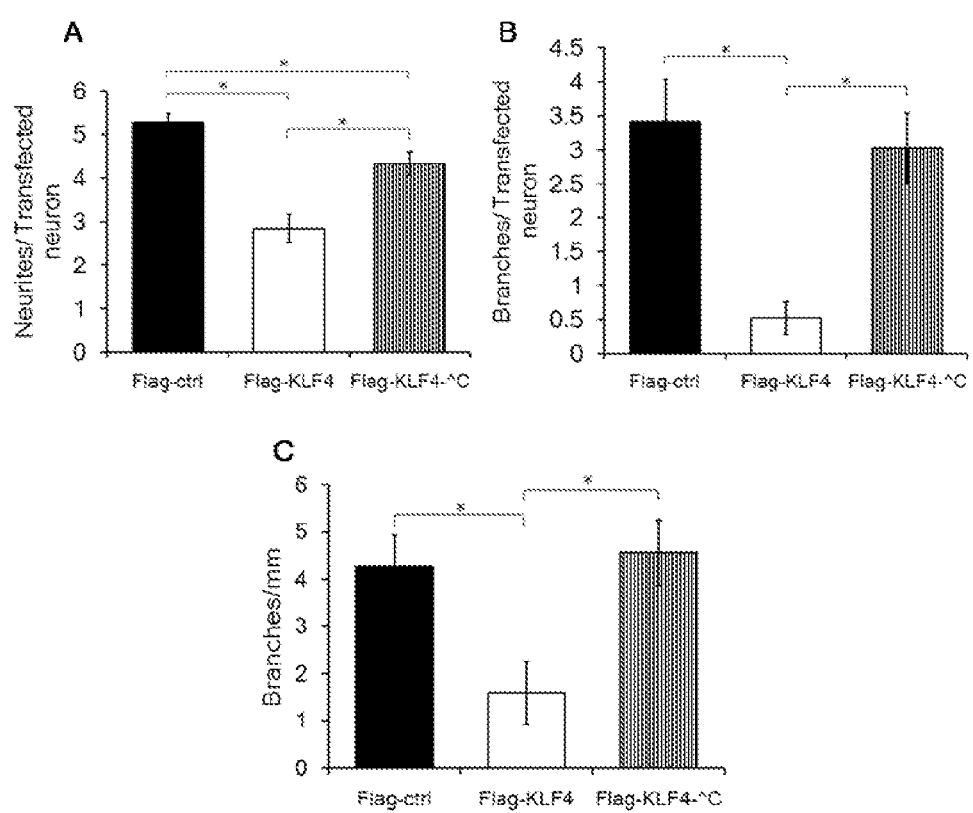

FIG. 10. KLF4 overexpression in embryonic RGCs decreases the numbers of both neurites and branches. E20 RGCs were purified and transfected using Lipofectamine 2000 with a FLAG control plasmid, FLAG-KLF4, or FLAG-KLF4-^C deletion mutant lacking the C-terminal zinc finger DNA-binding domain. Neurons were plated for 3 days on PDL- and laminin-coated plates in growth media. Following immunostaining, transfected neurons were imaged and hand-traced. KLF4 overexpression decreased the average number of neurites (A), branches (B), and branches normalized to total neurite length of each neuron (C), whereas RGCs overexpressing the truncated Flag-KLF4-^C behaved similarly to controls (p<0.01, unpaired t-test post-Bonferroni; n>25 for each; mean±SEM).

Figure 11:
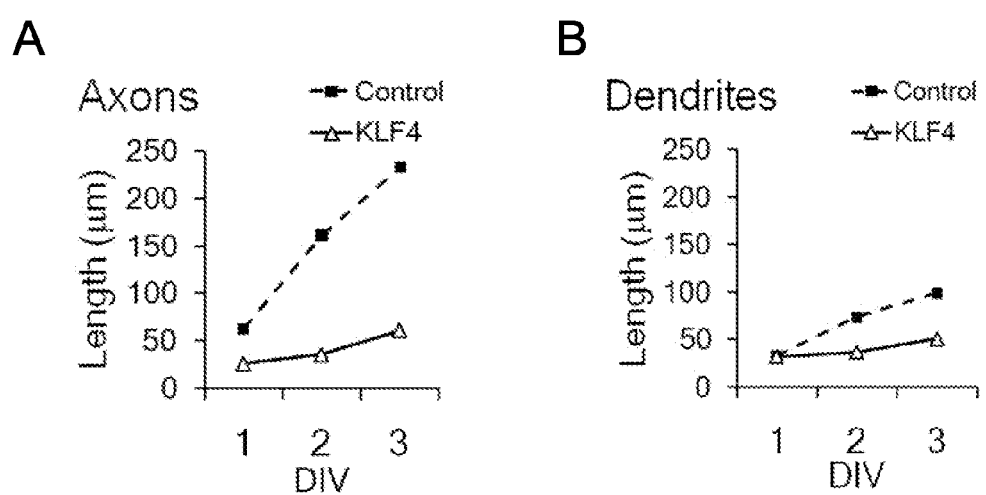

FIG. 11. RGCs overexpressing KLF4 continue to extend neurites, but at a slower rate. E20 RGCs were purified and transfected with either KLF4-pIRES2-eGFP or mCherry-pIRES2-eGFP and cultured for 1, 2, or 3 days (DIV) prior to immunostaining for tau. Hand tracing revealed that while KLF4 transfected cells have decreased growth ability, they are still able to grow over a period of days whether looking at the longest neurite (presumed axon, A) or all neurites (B) (p<0.001 day 1 to day 3 in each graph by unpaired t-test; n>70 in every condition).

Figure 12:
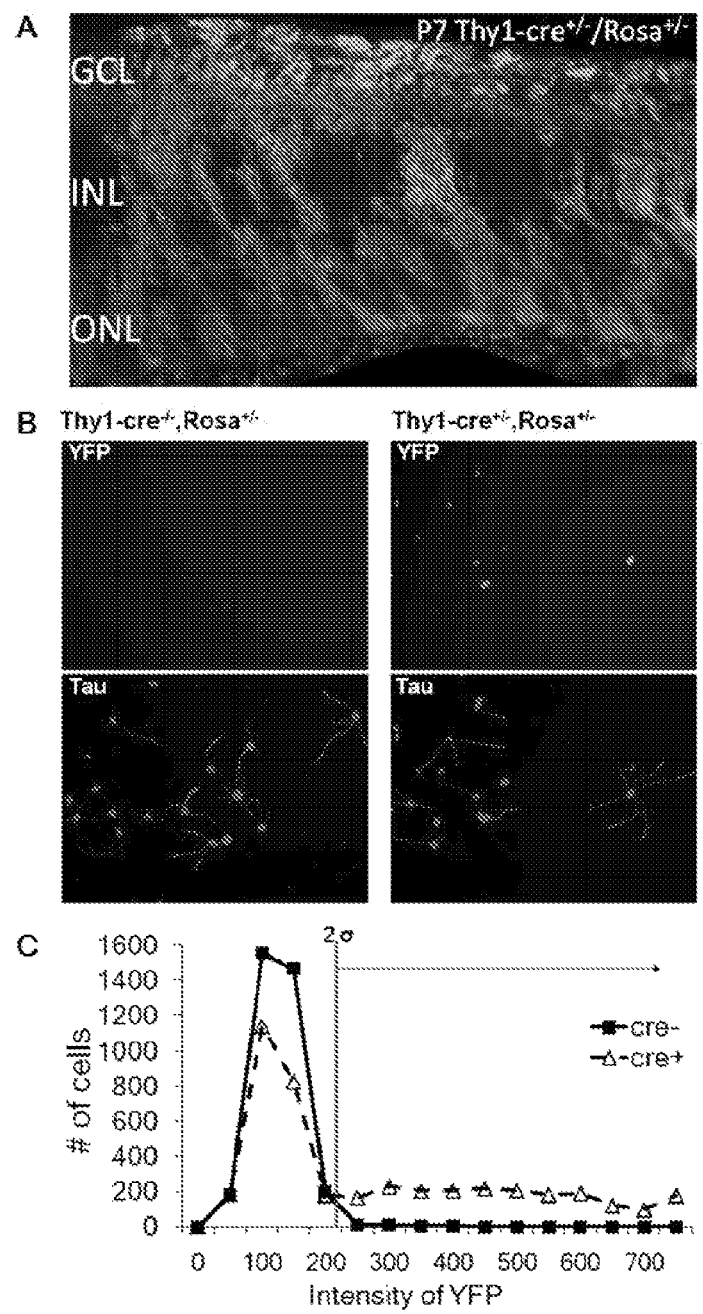

FIG. 12. Half of RGCs activate Cre in the Thy1-cre+/−/Rosa+/−mice. Alexa Fluor 594-labeled cholera toxin B was injected into the superior colliculus of P7 Thy1-cre+/−/Rosa+/−mice to retrogradely label RGCs (red). Eyes were fixed, sectioned and immunostained to amplify the EYFP signal (green). A) Retinal cross sections reveal that YFP was expressed in RGCs, as well as in other retinal cells. B) RGCs from P10 Thy1-cre+/−/Rosa+/− and Thy1-cre−/−/Rosa+/−mice were purified by immunopanning, cultured on PDL- and laminin for 3 days, and immunostained for tau (neurites) and GFP (to amplify YFP). Images were taken both with a Zeiss microscope and by the Cellomics Kineticscan software to determine intensity of YFP fluorescence. C) Two times the standard deviation of background intensity in Thy1-cre−/−/Rosa+/−RGCs yielded a baseline threshold for "YFP+". 46% of RGCs were YFP+, suggesting that this Thy1-cre line is targeting approximately half of immunopanned RGCs.

Figure 13:
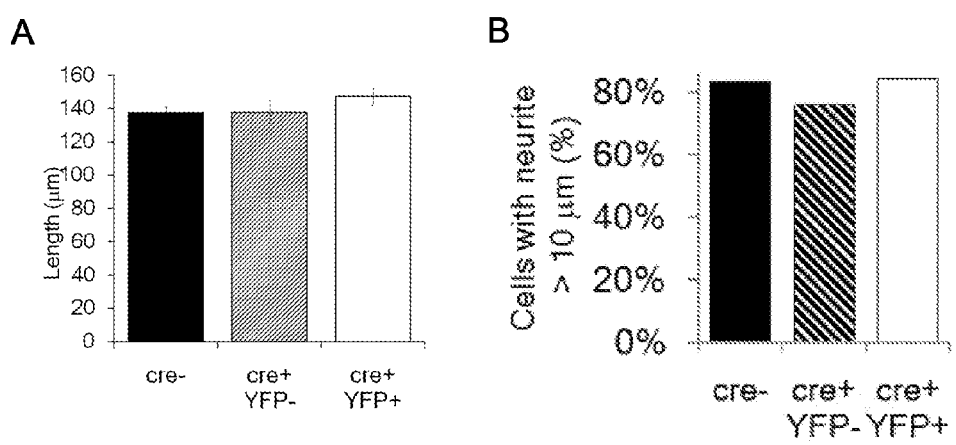

FIG. 13. Transgenic cre expression does not affect RGC neurite growth. RGCs from P10 Thy1-cre$^{+/-}$/Rosa$^{+/-}$ and Thy1-cre$^{-/-}$/Rosa$^{+/-}$ mice were purified by immunopanning, cultured on PDL and laminin for 3 days, and immunostained for Tau (neurites) and GFP (to amplify YFP). Cellomics Kineticscan software imaged and traced neurites, and measured YFP intensity. The baseline threshold of YFP intensity indicating cre targeting was determined as in Supplemental FIG. 5, above. RGCs were grouped either as all RGCs from Thy1-cre- animals (no Cre expression, black bars), YFP- cells from Thy1-cre+animals (also no Cre, hatched bars), or YFP+ cells from Thy1-cre+animals (Cre-expressing RGCs, white bars). Neurons with growth <10 μm were not included in this analysis. Quantification of total neurite length (A) or of percent of RGCs with at least one neurite >10 μm (B) revealed no differences between genotype (A: ANOVA revealed no significant differences between genotype; 1 representative experiment shown, n>2000 for each condition; mean ±SEM).

Figure 14:
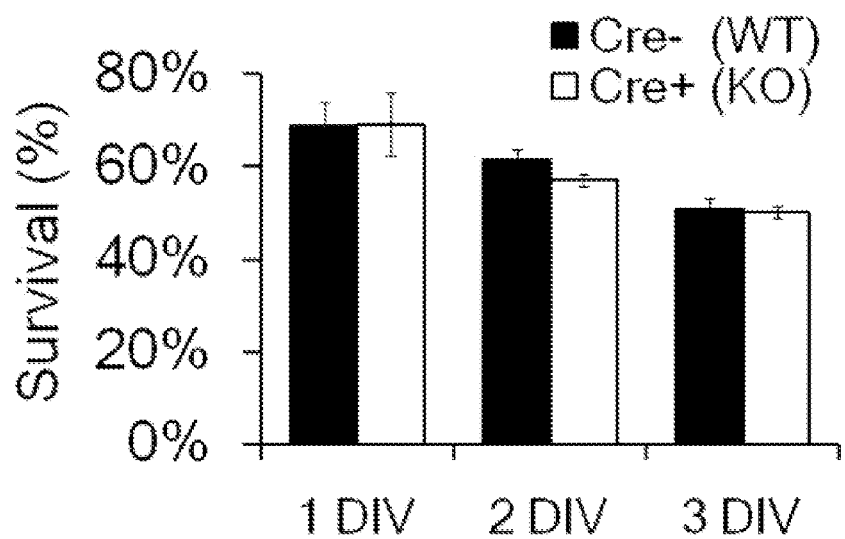

FIG. 14. KLF4 knockout does not affect survival of RGCs in vitro. Purified P12 RGCs were cultured from Thy1-cre$_{-/-}$/KLF4$_{fl/fl}$/Rosa+(Cre- WT) and Thy1-cre$_{+/-}$/KLF4$_{fl/fl}$/Rosa+(Cre+KO) mice. MTT survival assays at 1-3 DIV showed no significant differences in survival between KLF4 KO and WT RGCs (N=3; mean±SEM).

Figure 15:
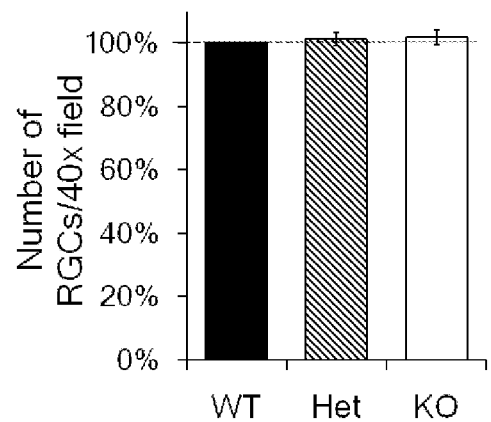

FIG. 15. KLF4 knockout during development does not affect adult RGC number or survival after injury. Two weeks after optic nerve crush of Thy1-cre$_+$/KLF4$_{+/+}$(WT), Thy1-cre$_+$/KLF4$_{fl/+}$(Het), and Thy1-cre$_+$/KLF4$_{fl/fl}$ (KO) mice, retinas from both the control eye (uninjured nerve) and injured eye (crushed nerve) were flatmounted and immunostained for βIII tubulin (Tuj 1) to label RGCs. Confocal imaging of retinas from knockout animals, normalized to WT, showed no differences in basal RGC number in the contralateral uninjured retinas (A; mean±SEM; n=8 WT, 4 Het, 9 KO) or in RGC survival two weeks after optic nerve crush (B; mean±SEM; n=6 WT, 4 Het, 9 KO).

Figure 16:
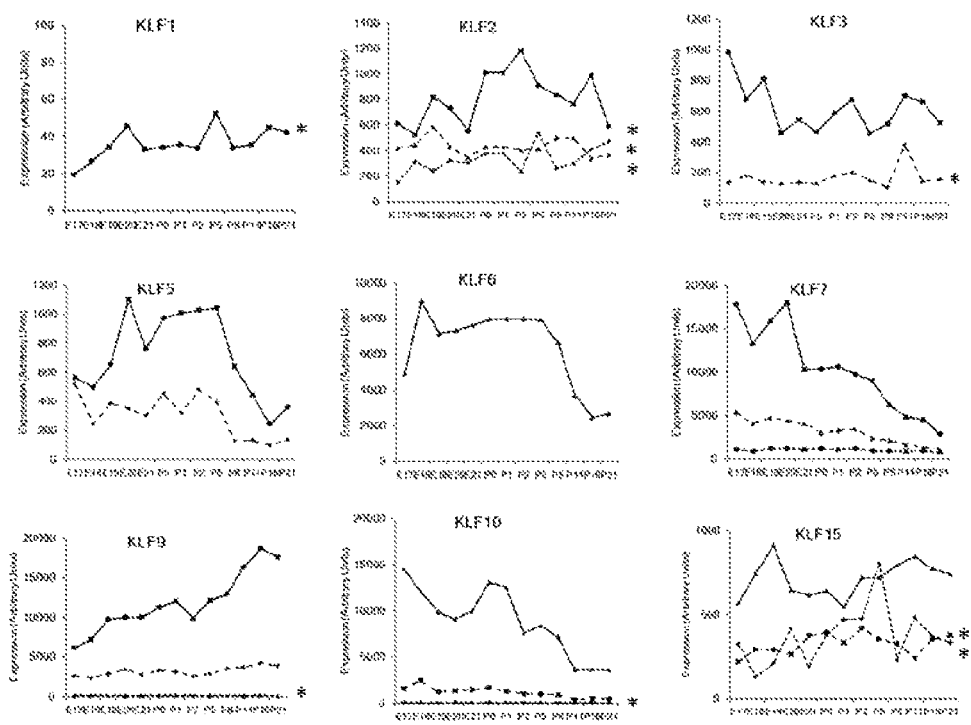

FIG. 16. Multiple KLFs are expressed in RGCs and are developmentally regulated. RNA was isolated from acutely purified RGCs from multiple ages and analyzed by microarray analysis on Affymetrix chips (1). 9 of 17 KLFs were probed on these arrays using between 1-3 probes; probes not present in at least 2 samples within one age by the Affymetrix algorithm are marked as "absent" with an asterisk at the end of the line. Occasionally one probe would not detect message while the other probe would, as often happens in microarray datasets. All of these KLFs except for KLF1 were detected in RGCs by RT-PCR (FIG. 6).

Figure 17:
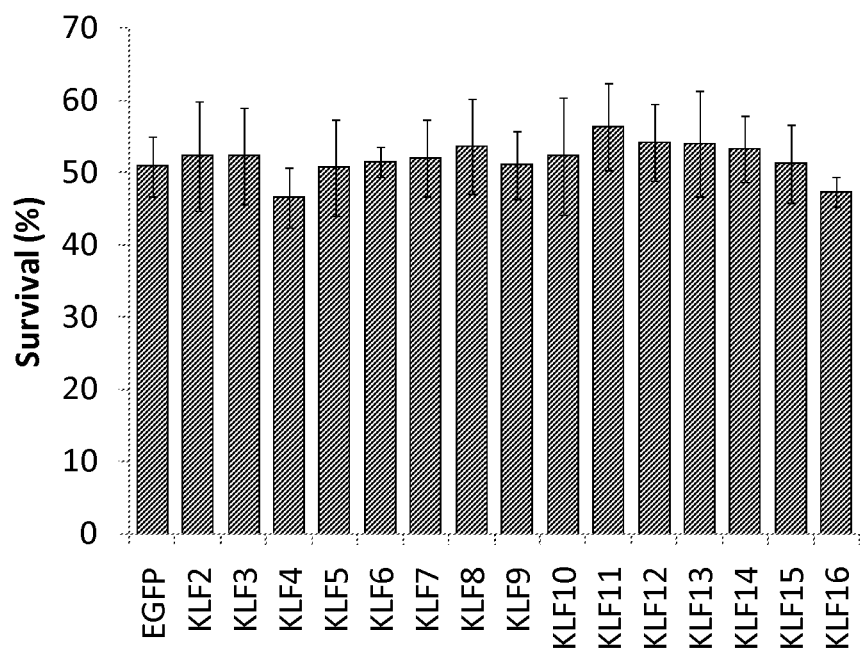

FIG. 17. Overexpression of KLF transcription factors does not affect cell survival. P5 cortical neurons were dissociated, transfected with EGFP or KLFs, and cultured on PDL- and laminin-coated plates in growth media. After 72 hours, the percent of cells that excluded SYTOX orange dye was quantified (Cellomics Kineticscan). Transfection with KLFs did not significantly change neuronal survival (p>0.50, ANOVA with Dunnett's post-test; N=3, n>500; mean±SEM).

Figure 18:
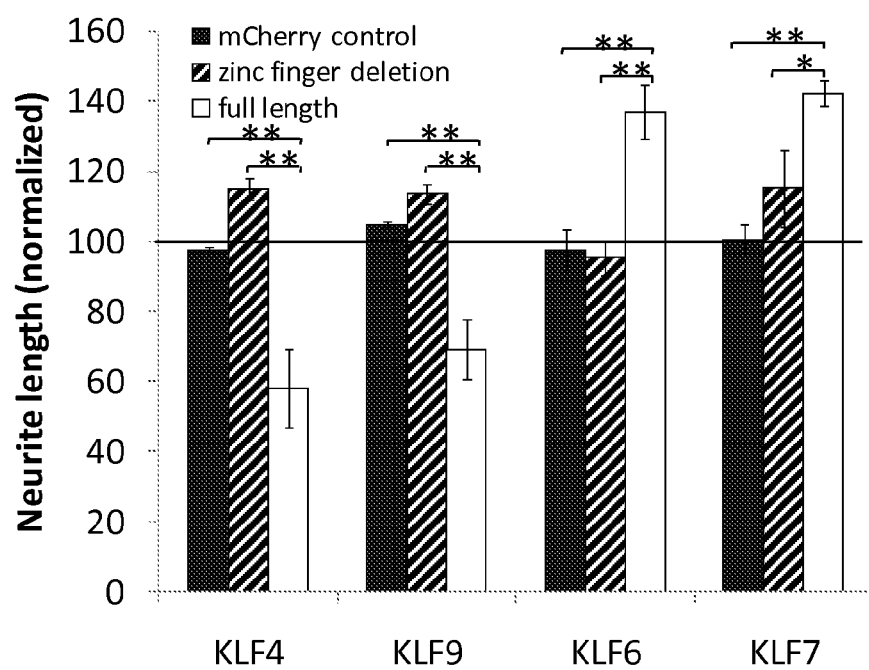

FIG. 18. KLF-mediated regulation of neurite length in cortical neurons requires the C-terminal zinc finger DNA-binding domain. mCherry control, full length KLF-IRES-mCherry, or zinc finger deletion KLF-ˆC—IRES-mCherry constructs encoding KLF4, -9, -6, or -7 were transfected into P5 cortical neurons. Neurons were plated for 3 days on laminin and immunostained for beta-III tubulin. Bars represent average total neurite length (Cellomics KSR) of transfected (mCherry+) neurons. Compared to mCherry control-transfected neurons, full length but not truncated KLFs significantly affected neurite lengths. (N=3, n>100; * p<0.05, ** p<0.01, ANOVA with post hoc Dunnett's test; mean±SEM).

Figure 19:
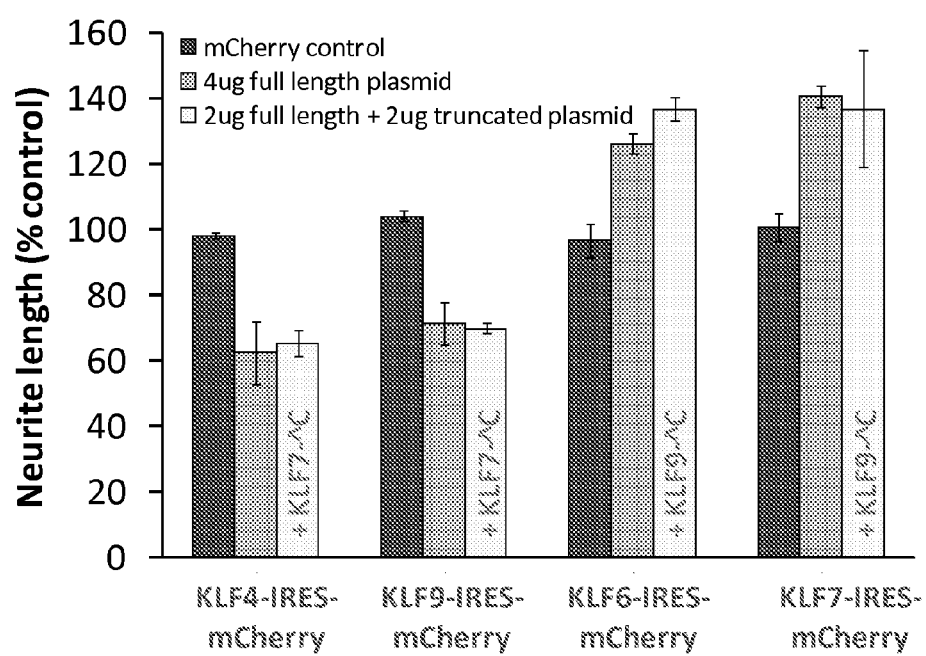

FIG. 19. Effect of KLFs in combinatorial experiments is independent of μg of plasmid transfected. 4 μg of control mCherry, 4 μg of full length KLF-IRES-mCherry, or 2 μg of full length KLF-IRES-mCherry plus 2 μg of truncated (nonfunctional, see FIG. 18) KLF-ˆC-IRES-mCherry were transfected into P5 cortical neurons. Neurons were plated for 3 days on laminin and immunostained for beta-III tubulin. Bars represent average total neurite length (Cellomics KSR) of transfected (mCherry+) neurons. Neurons transfected with 4 μg and 2 μg of functional KLFs had similar neurite lengths (N=3, n>100; p>0.05, ANOVA with post hoc Dunnett's test; mean±SEM).

SUMMARY

The present inventors used two independent methods to screen more than 900 genes that are developmentally regulated for their ability to regulate axon growth when overexpressed in neurons in culture. Remarkably, both screens identified closely related transcription factors from the Krüppel-like transcription factor (KLF) family as potent regulators of axon growth. There are 17 known members of the KLF family. The inventors expanded their studies to test the effect of overexpression of all 17 family members in neurons, and found that at least 11 family members (e.g., KLF 1, 2, 3, 4, 5, 9, 12, 13, 14, 15, and 16) potently suppress axon growth, while two family members (KLF 6 and 7) enhance axon growth. Furthermore, during the time in development when neurons lose the ability to regenerate axons in vivo, the inventors found that expression of the two growth-promoting family members declines 10-fold, while expression of at least two growth-suppressive KLFs increases.

The inventors used a transgenic approach to confirm that these in vitro effects also occur in animals. Mice were produced in which the growth-suppressive KLF4 gene was knocked out. These knockout mice exhibited improved axon regeneration after optic nerve injury.

In addition, a construct was generated in which the growth-enhancing KLF7 protein was over-expressed, under the control of the strong CMV promoter. When this construct was transfected into neurons in culture, increased axon lengths were observed. Similar results were found with a construct that causes KLF6 over-expression.

These findings inidcate that increasing the expression or activity of growth-promoting KLFs and/or decreasing the expression or activity of growth-suppressive KLFs can be used to enhance axon regeneration in an injured CNS.

One aspect of the invention is a method for promoting (e.g., stimulating, enhancing) CNS axon regeneration, comprising decreasing (inhibiting, suppressing) the expression or activity in a neuron of one or more of the members of the Krüppel-like transcription factor (KLF) family that suppress axon growth (e.g., KLF 1, 2, 3, 4, 5, 9, 12, 13, 14, 15 and/or 16). In addition to, or instead of, decreasing the expression or activity of the preceding KLF family members, a method of promoting CNS axon regeneration can comprise increasing (stimulating, enhancing) the expression or activity in a neuron of one or more of the members of the KLF family that promote axon growth (e.g., KLF 6 and/or 7). Because KLF family members may differ in the specifics of their effects in different populations of neurons, a method for promoting CNS axon regeneration may involve enhancing and/or stimulating different KLFs, or combinations of KLFs, according to the population of neurons that is involved.

For example, a method of the invention for promoting CNS axon regeneration can comprise contacting a neuron with an effective amount of an agent that inhibits the expression and/or activity in the neuron of one or more members of the KLF family that suppress axon growth (e.g., KLF 1, 2, 3, 4, 5, 9, 12, 13, 14, 15 and/or 16), and/or of an agent that stimulates (enhances) the expression and/or activity in the neuron of one or more of the members of the KLF family that promote axon growth (e.g., KLF 6 and/or 7). In one embodiment of the invention, a neuron is contacted with an effective amount of an agent that suppresses the expression and/or activity in the neuron of one or more of KLFs 1, 2, 3, 4, 5, 9, 12, 13, 14, 15 and/or 16. In another embodiment, the preceding method further comprises contacting the neuron with an effective amount of an agent that stimulates that expression and/or activity of KLF 6 and/or 7.

A method of the invention for promoting CNS axon regeneration can be performed in vitro (e.g., in cells such as cortical neurons, hippocampal cells, or retinal ganglion cells, in culture) or in vivo (in an animal, including a mammal, such as a laboratory animal, a domestic animal, a farm animal, a non-human primate, or a human). The in vitro methods are useful, e.g., for experimental studies, for screening for agents that modulate (increase or decrease) the expression or activity of a KLF family member, or the like. The in vivo methods are useful, e.g., for treating subjects, for preclinical or clinical evaluation of candidate KLF modulatory agents or treatments, or the like.

A variety of methods can be used to decrease (inhibit, suppress) the expression or activity in a neuron of one or more of the members of the Krüppel-like transcription factor (KLF) family that suppress axon growth. For example, the inhibition of expression can be achieved by contacting a neuron with, or administering to a suitable subject, an effective amount of an agent that inhibits transcription, translation or post-transcriptional or post-translational modification of a KLF family member of interest. In embodiments of the invention, the agent is a small molecule, or is an inhibitory nucleic acid, such as a small interfering RNA (siRNA), microRNA (miRNA), antisense oligonucleotide, ribozyme, etc. that is specific for a nucleic acid encoding or regulating the expression of the KLF family member. An inhibitory nucleic acid can specifically target a sequence that regulates expression of the gene (such as, e.g., a promoter) or it can target a coding sequence of the gene. Activity of the KLF proteins can be inhibited with, e.g., a dominant negative form of a KLF family member; a recombinant construct that expresses a dominant negative form of the protein; an antibody, active antibody fragment, or aptamer that is specific for the protein, etc.

A variety of methods can be used to stimulate or enhance the expression or activity in a neuron of one or more of the members of the Krüppel-like transcription factor (KLF) family that stimulate axon growth. For example, in one embodiment of the invention, the stimulation of expression can be achieved by contacting a neuron with, or administering to a suitable subject, an effective amount of an agent that stimulates transcription, translation or post-transcriptional or post-translational modification of a KLF family member of interest, such as an endogenous KLF gene or protein, or a KLF gene or protein that has been introduced exogenously. A stimulatory agent can specifically target a regulatory agent of the gene (such as, e.g., a promoter) or it can target a coding sequence of a gene or the protein translated from it. In other embodiments of the invention, the agent is a CNS axon regeneration-promoting KLF protein (such as KLF 6 and/or 7), or a nucleic acid that expresses the protein, which is administered directly (exogenously, e.g. by transfection, electroporation, or another suitable delivery method) to a neuron or subject. Studies presented herein show that such stimulatory proteins can interact with, and counteract the effects of, the growth-inhibitory KLF molecules. In one embodiment of the invention, the stimulatory protein is an active fragment of a regeneration-promoting KLF protein (such as KLF 6 and/or 7). An "active fragment" of a protein, as used herein, is a contiguous amino acid fragment of the protein that retains a biological function of the protein, such as its ability to stimulate CNS axon regeneration. In another embodiment of the invention, the stimulatory agent is a molecule that enhances the effect of a KLF stimulatory protein, for example by enhancing DNA binding or recruitment of co-factors. Suitable such agents will be evident to a skilled worker.

Another aspect of the invention is a method for identifying an agent (e.g., a small molecule, or an inhibitory nucleic acid such as an siRNA, miRNA, etc.) that promotes CNS axon regeneration, comprising screening candidate agents for their ability:

(1) to decrease (inhibit, suppress) the expression or activity (e.g., in a neuron) of one or more of the members of the Krüppel-like transcription factor (KLF) family that suppress axon growth (e.g., including but not limited to KLF 1, 2, 3, 4, 5, 9, 12, 13, 14, 15 and/or 16), and/or (2) to increase (stimulate, enhance) the expression or activity (e.g., in a neuron) of one or more of the members of the KLF family that promote axon growth (e.g., including but not limited to KLF 6 and/or 7).

Another aspect of the invention is a kit for treating a subject in need of CNS axon regeneration, comprising, optionally in one or more containers, a) an effective amount of an inhibitor of the expression and/or activity in a neuron of one or more of KLFs 1, 2, 3, 4, 5, 9, 12, 13, 14, 15 and/or 16, and, optionally, b) an effective amount of an agent that stimulates that expression and/or activity of KLF 6 and/or 7.

As used herein, the singular forms "a," "an," and "the" include plural referents unless the context clearly dictates otherwise.

An "effective amount," as used herein, refers to an amount that is sufficient to elicit a measurable amount of a biological activity of interest (e.g., a measurable amount of stimulation or inhibition of expression and/or activity of a KLF family member of the invention, of promotion of CNS axon regeneration, etc.).

When a method of the invention is carried out in vivo (in a subject), the subject can be any animal in which CNS axon regeneration is desirable, e.g. a mammal, such as an experimental animal, a farm animal, pet or the like. In some embodiments, the animal is a primate, including a human. In aspects of the invention, the animal has a condition or disease in which CNS axon tracts have been disrupted, such as, e.g., traumatic brain injury (e.g., traumatic optic neuropathy), stroke (including ischemic optic neuropathy), spinal cord injury, multiple sclerosis, macular degeneration, glaucoma, and other neurodegenerative diseases (e.g. Parkinson's Disease).

In a method of the invention, any of a variety of types of neurons can be contacted with a stimulatory or inhibitory agent. For example, the cells can be cortical neurons, optic neurons, hippocampal cells, or retinal ganglion cells. For in vitro assays, any of a variety of suitable cells lines can be used, which will be evident to a skilled worker. These include, e.g., cell lines which have relevant phenotypes similar to neurons, such as neurite-like outgrowth seen in, e.g., the N2A, PC12, or RGC5 cell lines.

Any of a variety of types of agents can be used to inhibit the expression or activity of a KLF family member in a method of the invention. An "inhibitor" of expression or activity is an agent that reduces the expression or activity by a detectable amount.

Methods for making and using suitable inhibitors are conventional and well-known in the art. Guidance in performing some of the methods of the invention is provided, for example, in Sambrook et al., *Molecular Cloning, A Laboratory Manual* (volumes Cold Spring Harbor Laboratory Press, USA or Harlowe and Lane, Antibodies a Laboratory Manual 1988 and 1998, Cold Spring Harbor Laboratory Press, USA. These and other references cited herein which provide guidance for performing methods related to the present invention are incorporated by reference herein in their entirety, specifically with regard to the method of making or using the method or modulatory agent.

In one embodiment of the invention, the inhibitory agent inhibits the expression of a KLF family member. The term "expression" of a gene, as used herein, refers to any aspect of the process by which information in a gene is converted to a functional molecule, e.g., any aspect of transcription or translation of the gene. For example, "expression" can refer to transcription, post-transcriptional processing, translation, or post-translational processing. Examples of inhibitors of expression include an antisense nucleic acid, a ribozyme, a microRNA, or a small interfering RNA (siRNA), wherein the inhibitor is specific for a nucleic acid encoding a KLF family member of interest, or an element that regulates its expression. By "specific for" a particular KLF family member is meant that the agent preferentially inhibits the expression of that KLF family member, compared to the expression of other genes. An agent that is specific for a particular sequence can bind preferentially to that sequence, under conventional conditions of high stringency.

Much of the discussion herein is directed to coding sequences of a KLF gene of interest. However, it is to be understood that this discussion also applies to non-coding sequences involved in the expression or regulation of expression of a gene, such as promoter sequences.

In one embodiment, the inhibitor is an antisense nucleic acid which comprises a single-stranded polynucleotide that is specific for a sequence encoding a KLF family member of interest, or a portion of one of those sequences. The nucleic acid sequences encoding the KLF family members described herein are well-known in the art. For example, one can access sequences encoding these proteins in publically available databases, such as the GenBank database operated by the NCBI.

A skilled worker would be able to design, make and use suitable antisense molecules, based on these sequences, without undue experimentation. The antisense nucleic acid may be, e.g., an oligonucleotide, or a nucleic acid comprising an antisense sequence that is operably linked to an expression control sequence, and that is expressed in the cell.

The use of antisense nucleic acids to downregulate the expression of a particular protein in a cell is well known in the art. See, e.g., Weintraub et al (1986) *Reviews—Trends in Genetics* 1(1); Askari et al. (1996) *N. Eng. J. Med.* 334, 316-318; Bennett et al. (1995) *Circulation* 92, 1981-1993; Mercola et al. (1995) *Cancer Gene Ther.* 2, 47-59; Rossi et al. (1995) *Br. Med. Bull.* 51, 217-225; or Wagner, R. W. (1994) *Nature* 372, 333-335. An antisense nucleic acid molecule may comprise a nucleotide sequence that is complementary to the coding strand of another nucleic acid molecule (e.g., an mRNA sequence), or to a portion thereof, and accordingly is capable of hydrogen bonding to the coding strand of the other nucleic acid molecule. Alternatively, antisense sequences can be complementary to a sequence found in the 5' or 3' untranslated region of the mRNA or a region bridging the coding region and an untranslated region (e.g., at the junction of the 5' untranslated region and the coding region). The antisense nucleic acid can be complementary in sequence to a regulatory region of the gene encoding the mRNA, for instance a transcription initiation sequence or regulatory element, or a splice site. In one embodiment, an antisense nucleic acid is designed so as to be complementary to a region preceding or spanning the initiation codon on the coding strand or in the 3' untranslated region of an mRNA. An antisense nucleic acid for inhibiting the expression of a protein of interest in a cell can be designed based upon the nucleotide sequence encoding the protein or upon sequences regulating its transcription or translation, constructed according to the rules of Watson and Crick base pairing.

For guidance in constructing antisense molecules that are complementary to a region of a gene involved in transcription (thereby blocking transcription and/or the production of isoforms, such as splice variants), see, e.g, Lee et al. (1979) *Nucl. Acids Res.* 6, 3073; Cooney et al. (1988) *Science* 241, 456; and Dervan et al. (1991) *Science* 251, 1360. For further guidance on administering and designing antisense, see, e.g., U.S. Pat. Nos. 6,200,960, 6,200,807, 6,197,584, 6,190,869, 6,190,661, 6,187,587, 6,168,950, 6,153,595, 6,150,162, 6,133,246, 6,117,847, 6,096,722, 6,087,343, 6,040,296, 6,005,095, 5,998,383, 5,994,230, 5,891,725, 5,885,970, and 5,840,708.

An antisense nucleic acid can exist in a variety of different forms. For example, it can be DNA, RNA, PNA or LNA, or chimeric mixtures or derivatives or modified versions thereof, single-stranded or double-stranded. The nucleic acid can be modified at the base moiety, sugar moiety, or phosphate backbone, using conventional procedures and modifications. Modifications of the bases include, e.g., methylated versions of purines or pyrimidines. Modifications may include other appending groups such as peptides, or agents facilitating transport across the cell membrane (see, e.g. Letsinger et al., 1989, *Proc. Natl. Acad. Sci. USA* 84:684-652; PCT Publication WO 88/09810 (1988), hybridization-triggered cleavage agents (e.g. Krol et al., 1988, *BioTechniques* 6:958-976) or intercalating agents (e.g., Zon, 1988, *Pharm. Res* 5:539-549).

Antisense nucleic acids (e.g., oligonucleotides) can be constructed using chemical synthesis procedures known in the art. Such an antisense nucleic acid can be chemically synthesized using naturally occurring nucleotides or variously modified nucleotides designed to increase the biological stability of the molecules or to increase the physical stability of the duplex formed between the antisense and sense nucleic acids, e.g. phosphorothioate derivatives and acridine substituted nucleotides can be used. To inhibit expression of a KLF family member of interest in cells in culture, such antisense nucleic acids can be added to cells in culture media. In one embodiment, synthetic oligonucleotides are added to a final concentration of about 10 nM to about 1000 nM, preferably about 50 nM to about 200 nM (e.g., about 200 µg oligonucleotide/ml).

Alternatively, an antisense nucleic acid can be produced biologically using an expression vector into which a nucleic acid has been subcloned in an antisense orientation (i.e., nucleic acid transcribed from the inserted nucleic acid will be of an antisense orientation to a target nucleic acid of interest). Expression control sequences (e.g., regulatory sequences)

operatively linked to a nucleic acid cloned in the antisense orientation can be chosen which direct the expression of the antisense RNA molecule in a cell of interest. For instance, promoters and/or enhancers or other regulatory sequences can be chosen which direct constitutive, tissue specific or inducible expression of antisense RNA. Inducible expression of antisense RNA, regulated by an inducible eukaryotic regulatory system, such as the Tet system (e.g., as described in Gossen et al. (1992) *Proc. Natl. Acad. Sci. USA* 89, 5547-5551; Gossen et al. (1995) *Science* 268, 1766-1769; PCT Publication No. WO 94/29442; and PCT Publication No. WO 96/01313) can be used. The antisense expression vector can be in the form of, for example, a recombinant plasmid, phagemid or attenuated virus. The antisense expression vector can be introduced into cells using standard techniques well known in the art. An antisense molecule of the invention can be complementary to any portion of the coding sequence of a KLF family member of interest, or a regulatory sequence thereof.

In another embodiment, an inhibitory agent of the invention is a ribozyme. Ribozymes are catalytic RNA molecules with ribonuclease activity which are capable of cleaving a single-stranded nucleic acid, such as an mRNA, to which they have a complementary region. For reviews on ribozymes see e.g., Ohkawa et al. (1995) *J. Biochem.* 118, 251-258; Sigurdsson et al. (1995) *Trends Biotechnol.* 13, 286-289; Rossi, J. J. (1995) *Trends Biotechnol.* 13, 301-306; Kiehntopf et al. (1995) *J. Mol. Med.* 73, 65-71). A ribozyme having specificity for an mRNA of interest can be designed based upon the nucleotide sequence of, e.g., the corresponding cDNA. For example, a derivative of a Tetrahymena L-19 IVS RNA can be constructed in which the base sequence of the active site is complementary to the base sequence to be cleaved in a VEGF-A or VEGF-A receptor mRNA. See for example U.S. Pat. Nos. 4,987,071 and 5,116,742, both by Cech et al. Alternatively, human VEGF-A or a VEGF-A receptor mRNA can be used to select a catalytic RNA having a specific ribonuclease activity from a pool of RNA molecules. See for example Bartel et al. (1993) *Science* 261, 1411-1418.

In another embodiment, the inhibitor is an siNA (a double-stranded nucleic acid, preferably an RNA, which is sometimes referred to as a small or short, interfering or inhibitory, nucleic acid. When the nucleic acid is an RNA, the molecule is sometimes referred to as an siRNA), used in a method of RNA interference to interfere with protein expression, and directed to a KLF family member of interest, or combinations thereof. Based on the well-known sequences of nucleic acids encoding these proteins, a skilled worker would be able to design, make and use any of a variety of suitable siNAs (e.g., siRNAs), based on these sequences, without undue experimentation. Typical examples of making and using siRNAs against KLF5, although for a purpose other than stimulating promoting axon regeneration, are described in US patent application 2009/0011003, which is incorporated by reference herein with respect to these methods and uses, and the sequences of the siRNAs.

As used herein, the term siNA is meant to be equivalent to other terms used to describe nucleic acid molecules that are capable of mediating sequence specific RNAi (RNA interference), for example short (or small) interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), translational silencing, and others. Long double-stranded interfering RNAs, such as miRNAs, appear to tolerate mismatches more readily than do short double-stranded RNAs. In addition, as used herein, the term RNAi is meant to be equivalent to other terms used to describe sequence-specific RNA interference, such as post-transcriptional gene silencing, or epigenetics. For example, siNA molecules of the invention can be used to epigenetically silence genes at both the post-transcriptional level or the pre-transcriptional level. In a non-limiting example, epigenetic regulation of gene expression by siNA molecules of the invention can result from siNA mediated modification of chromatin structure to alter gene expression (see, for example, Allshire (2002) *Science* 297, 1818-1819; Volpe et al. (2002) *Science* 297, 1833-1837; Jenuwein (2002) *Science* 297, 2215-2218; and Hall et al. (2002) *Science* 297, 2232-2237.)

An siNA can be designed to target any region of the coding or non-coding sequence of a gene. An siNA is a double-stranded polynucleotide molecule comprising self-complementary sense and antisense regions, wherein the antisense region comprises nucleotide sequence that is complementary to nucleotide sequence in a target nucleic acid molecule or a portion thereof and the sense region has a nucleotide sequence corresponding to the target nucleic acid sequence or a portion thereof. The siNA can be assembled from two separate oligonucleotides, where one strand is the sense strand and the other is the antisense strand, wherein the antisense and sense strands are self-complementary. The siNA can be assembled from a single oligonucleotide, where the self-complementary sense and antisense regions of the siNA are linked by means of a nucleic acid based or non-nucleic acid-based linker(s). The siNA can be a polynucleotide with a hairpin secondary structure, having self-complementary sense and antisense regions. The siNA can be a circular single-stranded polynucleotide having two or more loop structures and a stem comprising self-complementary sense and antisense regions, wherein the circular polynucleotide can be processed either in vivo or in vitro to generate an active siNA molecule capable of mediating RNAi. The siNA can also comprise a single-stranded polynucleotide having nucleotide sequence complementary to nucleotide sequence in a target nucleic acid molecule or a portion thereof (or can be an siNA molecule that does not require the presence within the siNA molecule of nucleotide sequence corresponding to the target nucleic acid sequence or a portion thereof), wherein the single-stranded polynucleotide can further comprise a terminal phosphate group, such as a 5'-phosphate (see for example Martinez et al. (2002) *Cell* 110, 563-574 and Schwarz et al. (2002) *Molecular Cell* 10, 537-568), or 5',3'-diphosphate. In certain embodiments, the siNA molecule of the invention comprises separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der waals interactions, hydrophobic interactions, and/or stacking interactions.

As used herein, siNA molecules need not be limited to those molecules containing only RNA, but further encompasses chemically-modified nucleotides and non-nucleotides. In certain embodiments, the short interfering nucleic acid molecules of the invention lack 2'-hydroxy (2'-OH) containing nucleotides. In certain embodiments, short interfering nucleic acids do not require the presence of nucleotides having a 2'-hydroxy group for mediating RNAi and as such, short interfering nucleic acid molecules of the invention optionally do not include any ribonucleotides (e.g., nucleotides having a 2'-OH group). Such siNA molecules that do not require the presence of ribonucleotides within the siNA molecule to support RNAi can however have an attached linker or linkers or other attached or associated groups, moieties, or chains containing one or more nucleotides with 2'-OH groups. Optionally, siNA molecules can comprise ribonucleotides at about 5, 10, 20, 30, 40, or 50% of the nucleotide positions. The modified short interfering nucleic acid molecules of the invention can also be referred to as short interfering modified oligonucleotides "siMON." Other chemical modifications, e.g., as described in PCT/US03/05346 and PCT/US03/05028, can be applied to any siNA sequence of the invention.

In one embodiment, an RNA interference molecule has a 2 nucleotide 3' overhang. If the RNA interference molecule is expressed in a cell from a construct, for example from a hairpin molecule or from an inverted repeat of the desired KLF sequence, then the endogenous cellular machinery will create the overhangs.

Considerations to be taken into account when designing an RNAi molecule include, e.g., the sequence to be targeted, secondary structure of the RNA target and binding of RNA binding proteins. Methods of optimizing siRNA sequences will be evident to the skilled worker. Typical methods are described, e.g., in Vickers et al. (2003) *J Biol Chem* 278, 7108-7118 and Yang et al. (2003) *Proc Nati Acad Sci USA* 99, 9942-9947.

Methods of making siNAs (e.g., siRNAs) are conventional and will be evident to the skilled worker. In vitro methods include, e.g., processing a KLF family member ribopolynucleotide sequence in a cell-free system (e.g., digesting long double-stranded RNAs with RNAse III or Dicer), transcribing a recombinant double-stranded KLF family member DNA in vitro, and chemical synthesis of nucleotide sequences homologous to a KLF family member sequence. In vivo methods include, e.g., (1) transfecting DNA vectors into a cell such that a substrate is converted into siRNA in vivo; (2) expressing short hairpin RNAs from plasmid systems using RNA polymerase III (pol III) promoters; and/or (3) expressing short RNA from tandem promoters.

When synthesized in vitro, a typical 0.2 micromolar-scale RNA synthesis provides about 1 milligram of siRNA, which is sufficient, e.g., for about 1000 transfection experiments using a 24-well tissue culture plate format. In general, to inhibit expression of KLF family members in cells in culture, one or more siRNAs can be added to cells in culture media, for example to a final concentration of about 50-200 µg, preferably about 50 µg siRNA/ml.

Any of a variety of conventional methods can be used to introduce nucleic acids, such as antisense nucleic acids or siNAs, into cells, including transfection, electroporation, or other methods known in the art. See, e.g., Hannon (2002) *Nature* 418, 244-251; Bernstein et al. (2002) *RNA* 7, 1509-1521; Hutvagner et al., *Curr. Opin. Genetics & Development* 12, 225-232; Brummelkamp (2002) *Science* 296, 550-553; Lee et al. (2002) *Nature Biotechnol* 20, 500-505; Miyagishi et al. (2002) *Nature Biotechnol.* 20, 497-500; Paddison et al. (2002) *Genes & Dev* 16, 948-958; Paul et al. (2002) *Nature Biotechnol.* 20, 505-508; Sui et al. (2002) *Proc. Natl. Acad. Sci. USA* 99, 5515-5520; and Yu et al. (2002) *Proc. Natl. Acad. Sci. USA* 99, 6047-6052. Nanoparticle methods such as those described by Schiffelers et al. (2004) *Nucleic Acid Res.* 32:e149 and fusion protein methods such as described by Song et al. (2005) *Nature Biotechnol.* 23:709-717 are also useful.

For further guidance concerning inhibitory RNAs, see e.g., Lau et al. (2003) *Scientific American*, pp. 34-41; McManus et al. (2002) *Nature Reviews Genetics* 3, 737-747; and Dykxhoorn et al. (2003) *Nature Reviews Molecular Cell Biology* 4, 457-467. For further guidance regarding methods of designing and preparing siRNAs, testing them for efficacy, and using them in methods of RNA interference (both in vitro and in vivo), see, e.g., Allshire (2002) *Science* 297, 1818-1819; Volpe et al. (2002) *Science* 297, 1833-1837; Jenuwein (2002) *Science* 297, 2215-2218; Hall et al. (2002) *Science* 297, 2232-2237; Hutvagner et al. (2002) *Science* 297, 2056-60; McManus et al. (2002) *RNA* 8, 842-850; Reinhart et al. (2002) *Gene & Dev.* 16, 1616-1626; Reinhart et al. (2002) *Science* 297, 1831; Fire et al. (1998) *Nature* 391, 806-811, Moss (2001) *Curr Biol* 11, R772-5, Brummelkamp et al. (2002) *Science* 296, 550-3; Bass (2001) *Nature* 411 428-429; and Elbashir et al. (2001) *Nature* 411, 494-498; U.S. Pat. No. 6,506,559; US patent application 20030206887; and PCT applications WO99/07409, WO99/32619, WO 00/01846, WO 00/44914, WO00/44895, WO01/29058, WO01/36646, WO01/75164, WO01/92513, WO 01/29058, WO01/89304, WO01/90401, WO02/16620, and WO02/29858.

Ribozymes and siRNAs can take any of the forms, including modified versions, described above for antisense nucleic acid molecules.

An antisense nucleic acid or siRNA may be of any length that is effective for inhibition of a gene of interest. Typically, an antisense nucleic acid is between about 6 and about 50 nucleotides (e.g., between about 10 and 30 nucleotides, or at least about 12, 15, 20, 25, 30, 35, 40, 45 or 50 nt), and may be as large as about 100 to about 200 nucleotides, or larger. Antisense nucleic acids having about the same length as the gene or coding sequence to be inhibited may be used. The length of an effective siRNA is generally between about 19 bp and about 29 bp in length, (e.g., about 19, 21, 23, 25, 27 or 29 bp), with shorter and longer sequences being acceptable.

In general it is preferable that an inhibitory nucleic acid, such as an antisense molecule, a ribozyme (the recognition sequences), or an siRNA, comprises a strand that is complementary (100% identical in sequence) to a sequence of a gene that it is designed to inhibit. However, 100% sequence identity between the nucleic acid and the target gene is not required to practice the present invention. Thus, the invention has the advantage of being able to tolerate naturally occurring sequence variations that might be expected due to genetic mutation, strain polymorphism, or evolutionary divergence. Alternatively, the variants may be artificially generated. Nucleic acid sequences with, e.g., small insertions, deletions, and single point mutations relative to the target sequence can be effective for inhibition.

The degree of sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than about 90% sequence identity (e.g., about 95%, 98% or 99%), or even 100% sequence identity, between the inhibitory nucleic acid and the portion of the target gene is preferred.

In one embodiment, an inhibitory nucleic acid of the invention hybridizes to the sequence it is intended to inhibit under conditions of high stringency. For example, the duplex region of an siRNA may be defined functionally as a nucleotide sequence that is capable of hybridizing with a portion of the target gene transcript under high stringency conditions (e.g., 400 mM NaCl, 40 mM PIPES pH 6.4, 1 mM EDTA, 70° C. hybridization for 12-16 hours, or equivalent conditions), followed generally by washing.

A skilled worker can readily test a candidate siRNA or antisense variant molecule to determine if it is inhibitory.

In another embodiment, the inhibitory agent inhibits an activity of a KLF family member. Examples of such inhibitors of activity (antagonists) include, e.g., an antibody specific for the KLF family member, a peptide or oligonucleotide which binds to the polypeptide of interest and effectively eliminates its function (an aptamer), or a small molecule pharmaceutical agent. Another potential antagonist is a closely related protein which binds to a KLF family member but inhibits its function rather than activating it. For example, an antagonist of a KLF family member could be a protein that is closely related to the family member, but is an inactive form of the polypeptide and thereby prevents the action of the family member. Examples of these antagonists include dominant negative mutants or forms of the protein. Methods for designing, making and using such molecules, including dominant negative molecules, are conventional and well-known to those of skill in the art.

One aspect of the invention is an antibody which is generated against a protein molecule or a peptide fragment of a KLF family member of interest. As used herein, the term "antibody" is used in the broadest sense and encompasses single monoclonal antibodies, polyclonal antibodies, chimeric antibodies, humanized antibodies, single-chain antibodies and antibody fragments (e.g., Fab, F(ab'), Fv). Antibodies are designed to block the activity of the family member. The terms a "blocking" antibody or a "neturalizing" antibody, as used herein, means an antibody that can inhibit the function of a defined target of interest. The antibodies can be produced by standard antibody technologies (e.g., monoclonal antibody technologies) and can be humanized if successful in blocking the KLF family member activity.

Another class of agents that inhibit the function of a KLF family member are small molecules which bind to and occupy the active site of the polypeptide, thereby making the catalytic suite inaccessible to substrate such the normal biological activity is prevented. Examples of small molecules include, e.g., small peptides or peptide-like molecules, and small organic compounds, which can include both synthetic compounds and naturally occurring compounds.

A number of inhibitors of the expression or the activity of KLF family members have been proposed and/or developed for the treatment of conditions other than CNS axon regeneration that are mediated by KLF proteins. Such treatments include, e.g., cancer therapy, pain modulation, stem cells, angiogenesis, including angiogenesis in the eye, and obesity. It is expected that such agents would also be effective to promote (stimulate, enhance) CNS axon regeneration. It might be necessary to modify the formulations, dosages and routes of administration of these agents in order to optimize the promotion of CNS axon regeneration. Suitable modifications would be evident to a skilled worker, using routine, conventional procedures. For example, suitable formulations are described in Remington's Pharmaceutical Sciences, 18th ed., Mack Publishing Company, 1990.

Among the agents that have been developed for treating KLF-mediated conditions other than those involving CNS axon regeneration are: antisense microRNAs (see e.g., US Patent application number 20090099123) or siRNA to Sp1 or CRSP protein subunit mRNAs to suppress the expression of Sp1 or CRSP protein subunits, and thus Sp1 target genes (see e.g., US Patent application number 20090138979), to treat cancers; oligonucleotide decoys comprising, e.g., a transcription factor binding site that binds to the KLF4 transcription factor (see e.g., US Patent application number 20080300209), to treat pain; agents that inhibit interactions between a KLF and MUC1 or the p53 promoter (see e.g., US Patent application number 20090098054), to treat cancers or inflammatory conditions; and an RNAi (e.g., a double stranded RNA or an RNA having a hairpin structure), that is complementary to a sequence of KLF5 mRNA, and that can be encapsulated in a liposome (see e.g., US Patent application number 20090011003). Methods described in these references can also be applied to designing and using additional KLF modulatory agents.

Any of a variety of agents can be used to increase (stimulate, enhance) the expression or activity in a neuron of one or more of the members of the KLF family that promote axon growth. For example, one can introduce agents (such as small molecules) which increase transcription, translation, or post-transcriptional or post-translational modification, of these KLF family members. Another method to promote CNS axon regeneration is to introduce into a neuron an effective amount of a KLF stimulatory protein (e.g., KLF 6 and/or 7), or a nucleic acid that expresses the protein, or a molecule that enhances the function of a KLF stimulatory protein, for example by enhancing DNA binding or recruitment of co-factors.

In one embodiment of the invention, the stimulatory agent is a KLF6 or KLF7 protein or a nucleic acid expressing it. Methods for making such constructs and introducing them into a cell, such as a neuron, are described elsewhere herein, e.g. with regard to antisense nucleic acids.

A number of considerations are generally taken into account in designing delivery systems, routes of administration, and formulations for inhibitory or stimulatory (modulatory) agents of the invention. The appropriate delivery system for a modulatory agent of the invention will depend upon its particular nature, the particular clinical application, and the site of drug action.

Among the methods which have been used successfully to deliver siRNAs are, e.g., plasmid vectors; retrovirus vectors, including oncoretrovirus vectors and lentivirus vectors; and hydrodynamic "high pressure" delivery.

In one embodiment of the invention, when treating a subject, a modulatory agent is administered by systemic intravenous (IV) or by a local intranasal route, such as an intranasal spray, a metered-dose inhaler, a nebulizer, or a dry powder inhaler. Formulations for delivery by a particular method (e.g., solutions, buffers, and preservatives, as well as droplet or particle size for intranasal administration) can be optimized by routine, conventional, empirical methods that are well-known in the art. For modulatory agents that are in the form of aerosol formulations to be administered via inhalation, the aerosol formulations can be placed into pressurized acceptable propellants, such as dichlorodifluoromethane, propane, nitrogen or the like.

The dose of an agent of the invention, or composition thereof, administered to an animal, particularly a human, in the context of the present invention should be sufficient to effect at least a detectable amount of a therapeutic response in the individual over a reasonable time frame (e.g., a CNS axon-regeneration effective amount). The exact amount of the dose will vary from subject to subject, depending on the species, age, weight and general condition of the subject, the severity or mechanism of any disorder being treated, the particular agent or vehicle used, its mode of administration and the like. The dose used to achieve a desired effect in vivo will be determined by the potency of the particular agent employed, the pharmacodynamics associated with the agent in the host, the severity of the disease state of infected individuals, as well as, in the case of systemic administration, the body weight and age of the individual. The size of the dose also will be determined by the existence of any adverse side effects that may accompany the particular inhibitory agent, or composition thereof, employed. It is generally desirable, whenever possible, to keep adverse side effects to a minimum.

Dosages for administration of an inhibitory or stimulatory agent of the invention can be in unit dosage form, such as a tablet or capsule. The term "unit dosage form" as used herein refers to physically discrete units suitable as unitary dosages for human and animal subjects, each unit containing a predetermined quantity of an inhibitor of the invention, alone or in combination with other suitable therapeutic agents, calculated in an amount sufficient to produce the desired effect in association with a pharmaceutically acceptable diluent, carrier, or vehicle.

The specifications for the unit dosage forms of the present invention depend on the particular agent of the invention, or composition thereof, employed and the effect to be achieved, as well as the pharmacodynamics associated with each polypeptide, or composition thereof, in the host. In some embodiments, the dose administered is a "CNS axon-regeneration effective amount."

One skilled in the art can easily determine the appropriate dose, schedule, and method of administration for the exact formulation of the composition being used, in order to achieve the desired response in the individual patient.

In embodiments of the invention, the expression or function of a plurality of KLF family members may be altered simultaneously. For example, one or more KLF family members may be suppressed, and simultaneously, one or more other family members may be enhanced. In one such embodiment, recombinant constructs are used which comprise a plurality of small hairpin RNAs that are concatenated on a vector which also may carry nucleic acid for expression of one or more KLF genes.

Another aspect of the invention is a method for identifying agents that can be used to promote CNS axon regeneration (e.g., to treat a subject in need of CNS axon regeneration). In one embodiment of the invention, the method comprises screening putative agents for their ability: (1) to decrease (inhibit, suppress) the expression or activity (e.g., in a neuron) of one or more of the members of the Krüppel-like transcription factor (KLF) family that suppress axon growth (e.g., including but not limited to KLF 1, 2, 3, 4, 5, 9, 12, 13, 14, 15 and/or 16), and/or (2) to increase (stimulate, enhance) the expression or activity (e.g., in a neuron) of one or more of the members of the KLF family that promote axon growth (e.g., including but not limited to KLF 6 and/or 7). Such a method can be carried out in vitro or in vivo, using any of the assays described herein, or others that will be evident to a skilled worker, for measuring axon regeneration. Any of the types of modulatory agents discussed herein, or others, can be tested in such a screening method. In one embodiment of the invention, screening for agents that decrease or increase the expression or activity of one or more members of the KLF family is performed in cell lines that have relevant phenotypes similar to neurons, such as neurite-like outgrowth seen in, e.g., N2A, PC12, or RGC5 cell lines.

In one embodiment of the invention, this method comprises contacting a suitable cell with a putative modulatory agent, and measuring the promotion of CNS axon regeneration (or the stimulation of a phenotype such as neurite-like outgrowth from cells such as N2A, PC12, or RGC5 cells), compared to that in a control cell which has not been contacted with the agent. A statistically significant increase in the treated cells compared to the control cells is indicative that the putative agent can be used to promote CNS axon regeneration.

Another aspect of the invention is a kit useful for performing any of the methods disclosed herein (e.g., for treating a subject in need of CNS axon regeneration), comprising a) an effective amount of an agent that suppresses the expression and/or activity in a neuron of one or more of KLFs 1, 2, 3, 4, 5, 9, 12, 13, 14, 15 and/or 16, and/or b) an effective amount of an agent that stimulates that expression and/or activity of KLF 6 and/or 7.

In one embodiment, the kit comprises an effective amount of an agent that suppresses the expression and/or activity in a neuron of one or more of KLFs 1, 2, 3, 4, 5, 9, 12, 13, 14, 15 and/or 16, and, optionally, an effective amount of an agent that stimulates that expression and/or activity of KLF 6 and/or 7.

The kit may also comprise, optionally, reagents or devices for introducing a modulatory agent into the subject. In one embodiment, the kit comprises components for delivering agents intended to stimulate (promote) regeneration of axons, or specific formulations that are specific for, or optimal for, the regeneration of axons. Such components and formulations will be evident to a skilled worker.

A kit suitable for a therapeutic treatment in a subject may further comprise a pharmaceutically acceptable carrier and, optionally, a container or packaging material. Among other uses, kits of the invention can be used in experiments, e.g. to study mechanisms by which a KLF stimulates axon regeneration, etc. A skilled worker will recognize components of kits suitable for carrying out any of the methods of the invention.

Optionally, the kits comprise instructions for performing the method, and/or a notice in the form prescribed by a governmental agency regulating the manufacture, use or sale of pharmaceuticals or biological products (such as the FDA), which notice reflects approval by the agency of manufacture, use or sale for human administration. In addition, agents in a kit of the invention may comprise other therapeutic compounds, for combination therapy. Other optional elements of a kit of the invention include suitable buffers, pharmaceutically acceptable carriers, or the like, containers, or packaging materials. The reagents of the kit may be in containers in which the reagents are stable, e.g., in lyophilized form or stabilized liquids. The reagents may also be in single use form, e.g., in single dosage form for use as therapeutics, or in single reaction form for diagnostic use.

In the foregoing and in the following examples, all temperatures are set forth in uncorrected degrees Celsius; and, unless otherwise indicated, all parts and percentages are by weight.

EXAMPLES

Example I

Materials and Methods

Constructs for Transfection

For the screen in hippocampal neurons, constructs in pEXPRESS-1, pSPORT or pCMV-SPORT6 (Open Biosystems) were co-transfected with pMAX (EGFP, Amaxa), and compared to an empty vector/pMAX co-transfection. The purchased constructs for the screen were full-length rat cDNAs (19/111, 17%), or else mouse (73%) or human (10%) when the full-length rat cDNA was unavailable.

Flag-tagged KLF4 constructs in a CS2+ vector were a generous gift of Chunming Liu (Univ of Texas). The flag control vector was purchased from Genecopoeia. Mouse KLF4 (Open Biosystems) and mCherry (gift of Roger Tsien, UCSD) were cloned into the pIRES2-eGFP vector (Clontech).

KLFs -1, -4, -5, -6, -7, -10, -12, -15, and -17 were obtained from Open Biosystems. KLF2 was a kind gift from Jerry Lingrel, Univ. of Cincinnati. The open reading frame of KLF9 was cloned from postnatal rat cortex, and KLFs -3, -8, -11, -13, -14, and -16 were cloned from mouse spleen or testis. All 17 KLFs were cloned into the CMV-pSPORT6 expression vector. pMAX (eGFP, Amaxa), or mCherry-pCMV-Sport6 were used as reporters in co-transfection experiments in cortical neurons.

For combinatorial experiments, the EGFP coding region of pIRES2-EGFP was replaced with mCherry. KLFs 4, -6, -7, and -9, and truncated versions that lacked the C-terminus zinc finger domain but maintained the adjacent NLS were cloned into both the IRES-EGFP and IRES-mCherry plasmids.

Culture and Transfection of Primary Neurons

Hippocampal Neurons—Embryonic day 18 (E18) rat hippocampi (Brainbits, LLC) were placed into Hibernate E media (Brainbits, LLC) containing 0.25% trypsin and 0.008% DNAse for 15 min at 37 deg C., washed 5 times with Hibernate E containing B27 (1:50), and triturated with variable sized fire-polished pipettes. Cells (500,000/tube) were pelleted (5 min, 80 g), resuspended in Rat Neuron Nucleofector solution (Amaxa) containing 3.5 µg DNA, and electroporated (Amaxa, program G-13). Immediately following transfection, 500 µl of growth media (see below) were added to transfected cells. Cells were plated onto PDL- and laminin-coated plates. A full media change was performed 4 hours following transfection. Transfection efficiencies were typically ~60%, and co-transfection efficiencies using 3 µg "gene-of-interest" DNA/0.5 µg reporter DNA were typically ~99%.

RGCs—Lipofectamine Transfection —400,000 embryonic RGCs purified by immunopanning (Chen et al. (1995) *Proc Natl Acad Sci USA* 92, 7287; Bregman et al. (1989) *J Comp Neurol* 282, 355), were incubated with 2 µl Lipofectamine 2000 (Invitrogen) and 0.8 µg DNA for 15 min at 37 deg C., and then plated on PDL- and laminin-coated plates in RGC media (see below, Chen et al. (1995), supra). A full media change was performed 4 hours following transfection. Transfection efficiencies were typically ~2%.

Electroporation—100,000 postnatal RGCs were purified by immunopanning. Final cell pellets were resuspended in an electroporation solution containing 2 µg of total DNA (GFP reporter and gene of interest), placed in a small cell number cuvette (Amaxa) and electroporated using Amaxa program SCN#1. Immediately following electroporation, growth media was added to the mixture and the whole solution placed into a small Eppendorf tube. RGCs were centrifuged for 16 minutes at 1800 rpm prior to resuspension and plating.

Cortical Neurons—Frontal cortex from P5 rats was dissociated sequentially in papain and trypsin. Dissociated cells were co-transfected with plasmid DNA-encoding KLFs and mCherry reporter at a 1:6 ratio, using electroporation in a 96-well format (Yiu et al. (2006) *Nat Rev Neurosci* 7, 617). Cells were plated in PDL- and laminin-coated 96-well plates in growth media conditioned overnight by astroglial cultures (Case et al. (2005) *Curr Biol* 15, R749). Transfection efficiencies were typically ~20%, and co-transfection efficiencies were typically >90%. For experiments combining KLFs, 2 µg of KLF-IRES-mCherry and 2 µg of KLF-IRES-EGFP plasmid were co-transfected. Only neurons that expressed both mCherry and EGFP were included in the analysis of neurite lengths.

Growth Media—The culture media for RGCs, hippocampal and cortical neurons was modified from Chen et al. (1995), supra, and included Neurobasal, penicillin/streptomycin, insulin (5 µg/ml), sodium pyruvate (1 mM), transferrin (100 µg/ml), BSA (100 µg/ml), progesterone (60 ng/ml), putrescine (16 µg/ml), sodium selenite (40 ng/ml), triiodothyronine (T3, 1 ng/ml), L-glutamine (1 mM), N-acetyl cysteine (NAC, 5 µg/ml), forskolin (5 mM) and B27 (Goldberg et al. (2002) *Science* 296, 1860). Media for RGCs and hippocampal neurons also contained BDNF (50 ng/ml) and CNTF (10 ng/ml); media for embryonic RGCs also contained GDNF (40 ng/ml); media for electroporated RGCs also contained both GDNF and bFGF (10 ng/ml).

Immunostaining

For cultured neurons, cultures were fixed using pre-warmed (37 deg C.) 4% paraformaldehyde (PFA). Following rinses in PBS, cultures were blocked and permeabilized in 20% normal goat serum (NGS)/0.02% triton X-100 in antibody buffer (150 mM NaCl, 50 mM Tris base, 1% BSA, 100 mM L-Lysine, 0.04% Na azide, pH 7.4) for 30 min to reduce non-specific binding. Cultures were incubated overnight at 4 deg C. in antibody buffer containing primary antibodies, washed with PBS, incubated in antibody buffer containing secondary antibodies and DAPI for 4 hours at room temperature, washed with PBS, and left in PBS for imaging.

For whole-mount staining, retinas from PFA-perfused animals were immunostained as above with the following modifications: all incubations were performed on a rocker, and the secondary antibody incubation was performed overnight at 4 deg C. Retinas were mounted in mounting medium with DAPI (Vectashield) on coverslips for confocal imaging.

Primary antibodies used for these experiments included anti-Tau (1:200, Sigma, T6402) anti-FLAG (1:750, F1804, Sigma), anti-GFP (1:600, Ayes Labs, GFP-1020), anti-MAP2 (1:10,000, Abcam, ab5392; 1:150, Sigma, M1406), anti-Turbo GFP (1:10,000, Evrogen, AB513), and anti-beta-III-tubulin (Tuj 1, 1:400, Covance, MMS-435P; 1:500, Sigma, T3952). Secondary antibodies were Alexa Fluor-488, -594, or -647-conjugated, highly cross-adsorbed antibodies (Invitrogen).

Quantification of Neurite Length

For "High Content Analysis" (also called High Content Screening, or HCS) of neuronal morphology, including neurite length, dendrite length, neurite number and neurite branching, automated microscopes (Cellomics KSR or VTI) and image analysis software (Cellomics BioApplications) were used to image and trace neurons using a 5× or 10× objective following immunostaining. Cortical neurons were traced using βIII tubulin immunoreactivity to visualize neurites. RGCs were traced using antibody-amplified EGFP signal, which filled transfected neurites. In the case of RGCs, neurons with dim EGFP label in neurites were excluded from analysis, due to frequent tracing errors of faint processes; the threshold for exclusion was established using a population of control neurons. Images and tracing were spot-checked to verify that the algorithms were correctly identifying neurites and quantifying growth.

For those experiments requiring hand tracing, including confirmations of automated quantification, surviving neurons were identified by nuclear morphology and DAPI intensity and imaged in multiple fluorescent channels using a Zeiss Axiovert 200M microscope. Hand tracing was performed using Axiovision software. MAP2+ neurites, which typically demonstrated thicker origins and tapering widths, were measured as dendrites; Tau+/MAP2− neurites, which typically demonstrated thinner, non-tapering profiles, were measured as axons.

Quantification of Neuronal Survival

Survival of neurons was determined using either an MTT (3-(4,5-dimethylthiazol-2-yl)-2,5-diphenyl tetrazolium bromide) assay (Blackmore et al. (2006) *J Neurobiol* 66, 348), identification of dead nuclei by the Cellomics software (see below), or Sytox staining. MTT (0.5 mg/ml) was applied to at least 3 wells per condition and incubated at 37 deg C. for 30 min. Surviving neurons produced a blue precipitate; dead neurons remained colorless. At least 3 wells per condition and multiple fields of view in identical well locations were counted for each sample using a grid overlay.

To determine survival using Cellomics HCS assays, DAPI nuclear staining morphology was used. Dead cells had a higher DAPI intensity per pixel and smaller nuclei; surviving cells had low DAPI fluorescence intensity per pixel and a larger nucleus. Multiple fields of view per well were counted for each sample, with a typical replicate being 6 wells within an experiment.

Cortical neuron survival after transfection was measured by simultaneous Hoechst and Sytox orange dye staining at 1 or 3 days after plating. Hoechst+/Sytox− (surviving) cells were quantified with the Cellomics KSR, with a minimum of 500 cells counted per treatment.

Quantitative Reverse Transcription Polymerase Chain Reaction (qRT-PCR)

RGCs were purified by immunopanning as above and the pellet from the final centrifugation (before any cell culture) was snap frozen in liquid nitrogen. In most cases, multiple pellets (preps) were combined for each sample. RNA was purified (RNeasy, Invitrogen), subjected to reverse transcription (RT, iScript, Bio-Rad), and the resulting cDNA was used as the template for a quantitative-PCR reaction (Sybr green, Bio-Rad) performed on an iCycler (Bio-Rad) with KLF-X and 18S primers. In most tests, 6 repeat wells (technical replicates) were used for each condition. "No RT" control samples were also tested. To determine fold change, an efficiency analysis was performed for each tissue type in combination with the specific primers being tested. Dilutions of a sample were made for 1:10, 1:100, and 1:1000, and the threshold counts graphed as a line, with the slope being used for the efficiency formula (Dusart et al. (1997) *J Neurosci* 17, 3710). Each experiment was performed 2-3 times with different pools of RNA (biological replicates).

For non-quantitative RT-PCR, RGC RNA was purified and reverse-transcribed as described above. 1 µl of cDNA was used as a template for each PCR reaction (Phusion, NEB). 5 µl of this product was run on a 2% agarose gel containing Gel Red (Biotium, Hayward Calif.), and visualized using Gene Genius gel documentation system (Syngene, Frederick, Md.). The experiment was repeated to confirm initial band expression using RNA from a separate set of animals (biological replicates).

Primers used for genotyping N-Tg(Thy1-cre)1Vln/J mice (Jackson Laboratories) and Gt(ROSA)26Sor$^{tm1(eYFP-Cos)}$ mice (Jackson Laboratories), were according to the Jackson Laboratories recommendations (available on their website), as follows:

```
Cre -
                                       (SEQ ID NO: 1)
oIMR0042 ctaggccacagaattgaaagatct, (SEQ ID NQ: 2)
oIMR0043 gtaggtggaaattctagcatcatcc, (SEQ ID NO: 3)
oIMR1084 gcggtctggcagtaaaaactatc, (SEQ ID NO: 4)
oIMR1085 gtgaaacagcattgctgtcactt;

Rosa -
                                       (SEQ ID NO: 5)
oIMR0316 ggagcgggagaaatggatatg, (SEQ ID NO: 6)
oIMR0883 aaagtcgctctgagttgttat, (SEQ ID NO: 7)
oIMR4982 aagaccgcgaagagtttgtc.
``` fKLF4 mice were genotyped as described (Bouslama-Oueghlani et al. (2003) *J Neurosci* 23, 8318). The rd mutation was assayed through genotyping as described (Li et al. (1995) *Eur J Neurosci* 7, 1164). For qRT-PCR, primers for KLF4 were as described (Cai et al. (2001) *J Neurosci* 21, 4731); for rat KLF6 were forward: gagttcctcggtcatttcca (SEQ ID NO:8), reverse: tgctttcaagtgggagcttt (SEQ ID NO:9); for rat KLF7 were forward: ttgctctctcgggacaagtt (SEQ ID NO:10), reverse: gagctgagggaagccttctt (SEQ ID NO:11); for rat KLF9 were forward aacaaataccgacccatcca (SEQ ID NO:12), reverse: agactttcccacagccactg (SEQ ID NO:13). For RT-PCR, primers for KLF1-KLF13 and KLF15-17 were as described (Gao et al. (2004) *Neuron* 44, 609) and for KLF14 were as described (Chen et al. (1997) *Nature* 385, 434).

Animals

All use of animals conformed to the ARVO Statement for the Use of Animals in Research, and was approved by the Institutional Animal Care and Use Committee and the Institutional Biosafety Committee of the University of Miami.

Sprague-Dawley rats of varying ages were obtained from Harlan Laboratories.

Mice were bred from the following strains: floxed KLF4 (fKLF4) mice (Bouslama-Oueghlani et al. (2003), supra), B6.129X1-Gt(ROSA)26Sor$^{tm1(eYFP)Cos}$/J (Stock #006148, Jackson Laboratory), and FVB/N-Tg(Thy1-cre)1Vln/J (Stock#006143, Jackson Laboratory). The Thy1-cre background strain, FVB, was homozygous for retinal degeneration (rd) mutations, and this mutation was bred out using C57BL/6J as detected through genotyping (Li et al. (1995), supra). Once the rd mutation was bred out, we spot checked the rd genotype to confirm periodically that the mutation was absent.

Intraorbital Optic Nerve Crush and Intravitreal Injection

For all in vivo experiments, optic nerve crush, tissue processing, imaging and analysis were performed masked, such that the experimenters did not know the genotype of the animal at any stage until the analysis was complete. In separate experiments looking at shorter term post-crush survivals, we saw no spared axons greater than 0.2 mm beyond the crush site (Y. Hu, A. Peterson, J. Bixby and J. Goldberg, data not shown). In this manuscript, any axon sparing would be expected to be distributed randomly between groups, due to the masked design.

8-12 week old Thy1-cre$^+$/KLF4$^{+/+}$, Thy1-cre$^+$/KLF4$^{fl/+}$, Thy1-cre$^+$/KLF4$^{fl/fl}$ littermate mice were used for optic nerve crush experiments. Following induction of anesthesia, the left intraorbital optic nerve was surgically exposed, the dural sheath was opened longitudinally, and the nerve was crushed 1 mm behind the eye with angled jeweler's forceps (Dumont #5) for 10 sec, avoiding injury to the ophthalmic artery. Nerve injury was verified visually at the crush site, while the vascular integrity of the retina was evaluated by fundoscopic examination. Mice with any significant postoperative complications (e.g., retinal ischemia, cataract) were excluded from further analysis. For anterograde axon labeling, intravitreal injections of 1 µl cholera toxin subunit B (CtB594, 10 µg/µl; Molecular Probes) were performed just posterior to the pars plana with pulled glass pipette connected to a 50 µl Hamilton syringe. Care was taken not to damage the lens. One day later, at 2 weeks after the crush injury, mice were deeply anaesthetized and perfused with 4% PFA in 0.1 M phosphate buffer. Optic nerves and retinas were dissected and post-fixed in 4% PFA for one hour and subsequently washed in PBS. Optic nerves were incubated in 30% sucrose at 4 degrees overnight prior to mounting in OCT. Longitudinal sections (16 µm) were made of the entire optic nerve. All sections with an apparent crush site and CtB labelling were imaged with a 20× objective. Pictures were taken, starting with the furthest regenerating axons and working backwards toward the crush site. Lines were drawn perpendicular to the long axis of the optic nerve 0.2, 0.3, 0.5, 0.75, 1, and 1.5 past the crush site (as applicable), and CtB+ axons between these lines were counted. Analysis of the total sum of regenerating fibers from all sections for each animal were performed as well as the average number of axons at each measurement location/distance per number of sections. Using either analysis, the data yielded the same results.

Statistical Analysis. Distance and fiber-sum data were log transformed to effect linearity (a basic assumption of the statistical tests used) and approximate normality of residuals. As some fiber-sum measurements were zero, a small positive constant, 0.2, was added to all fiber-sum measurements prior to taking the logarithm. An analysis of covariance, with a mixed model component to account for multiple measurements in the same animals, was used to compare the distance relationship of fiber-sums by genotype between the groups. A second analysis in which zero values were excluded reached similar conclusions.

Retinal Survival Quantification

Eyes were dissected from PFA-perfused animals and left in 4% PFA for an additional hour. Retinas were then dissected into PBS to await immunostaining. Whole-mount immunostaining was performed (see above) using anti-beta-III tubulin (Tuj 1) to visualize RGCs, and DAPI to detect nuclei. Retinas were mounted onto coverslips in mounting medium (Vectashield) and imaged on a Leica confocal microscope. Using a 40× oil objective, 4 stacked images were taken 2 fields of view from the optic disc in each perpendicular direction. RGCs were quantified by an observer masked to genotype using Metamorph software.

Example II

KLF Family Members Regulate Intrinsic Axon Regeneration Ability

Figure 1:
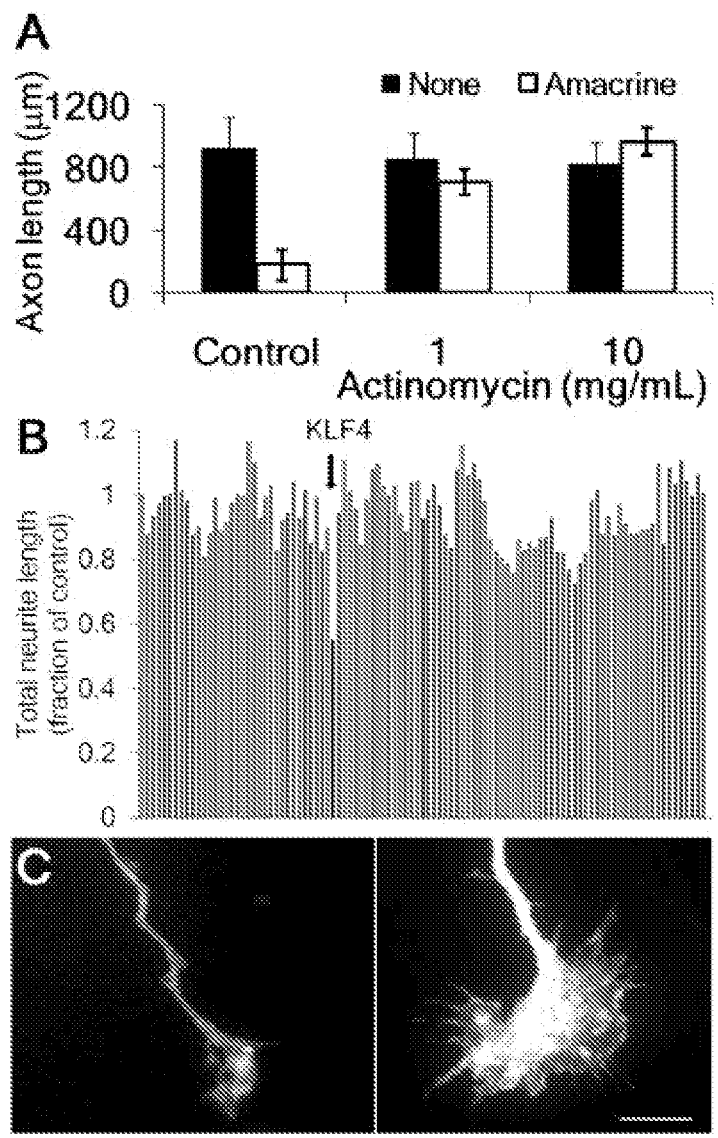
FIG. 1. A screen of developmentally regulated genes identifies KLF4 as an inhibitor of neurite growth. A) Purified embryonic RGCs were cultured in the presence (white bars) or absence (black bars) of amacrine cell membranes for 3 days, and replated away from amacrine cell membranes, after which RGC axon growth was measured. Actinomycin D blocked RGCs' decrease in axon growth caused by amacrine cell membranes (Mean±SEM). B-C) E18 hippocampal neurons were co-transfected with 111 candidate genes and EGFP, cultured for 3 days on laminin, and immunostained for Tau to visualize neurites. B) Neurite length of co-transfected (EGFP+) neurons. Bars represent average neurite length normalized to EGFP control (far left). KLF4 (arrow) decreased neurite growth by 50%. C) EGFP+ growth cones of EGFP+/KLF4 transfected neurons (right) are enlarged compared to control-transfected neurons (left). (Scale bar, 10 µm)

To investigate the molecular basis for the developmental loss of axon growth ability in RGCs, we took advantage of the fact that co-culture with amacrine cell membranes is sufficient to signal embryonic RGCs to decrease their rapid axon growth (Goldberg et al. (2002), supra). Addition of the transcriptional inhibitor actinomycin D blocked this effect of amacrine membranes, and embryonic RGCs retained their capacity for axon growth (FIG. 1A). These data suggest that gene transcription is required for the developmental loss of intrinsic axon growth ability in RGCs.

To identify candidate genes, we profiled gene expression from embryonic day 17 (E17) through postnatal day 21 (P21) RGCs (Wang et al. (2007), supra), spanning the period when axon growth ability declines in vivo (Goldberg et al. (2002), supra; Chen et al. (1997), supra). We screened 111 candidates whose expression changed greater than 3-fold by overexpression in embryonic hippocampal neurons, and used automated image acquisition and neurite tracing (KSR instrument, Cellomics) for rapid, unbiased quantification of neurite length (Buchser et al. (2006) *Biotechniques* 41, 619); the investigator (DLM) was blinded to gene identity until the screen was complete. The zinc-finger transcription factor, Krüppel-like factor-4 (KLF4), was the most effective suppressor of neurite outgrowth, decreasing average length by 50% (FIG. 1B). In a separate, blinded screen examining growth cone morphologies, KLF4 again emerged as the most interesting candidate gene as growth cones in KLF4-overexpressing hippocampal neurons were consistently enlarged (e.g. FIG. 1C).

Figure 2:
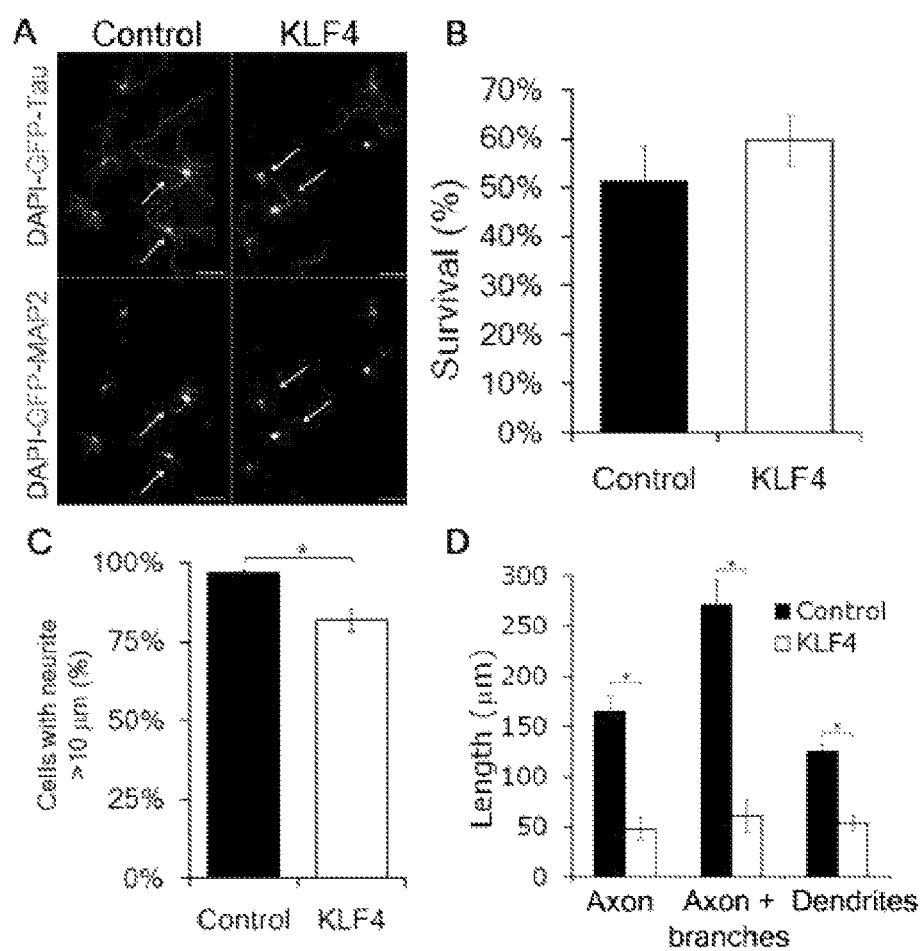
FIG. 2. KLF4 overexpression in hippocampal neurons decreases neurite growth and neurite initiation. A-D) E18 hippocampal neurons were co-transfected with KLF4 or control plus EGFP, cultured on laminin-coated plates, and immunostained for Tau (neurites) and MAP2 (dendrites). A) Transfected EGFP+ cells (arrows) were imaged to detect DAPI, EGFP, and either Tau (top) or MAP2 (bottom). KLF4-transfected neurons had shorter axons and dendrites. (Scale bar, 50 µm) B) There was no difference in survival by nuclear morphology and DAPI intensity between control- and KLF4-transfected neurons (Mean±SD). C) KLF4 overexpression decreased the percentage of transfected neurons that were able to extend at least 1 neurite >10 µm (N=5; * $p<0.01$, paired t-test; Mean±SEM). D) KLF4 overexpression decreased both axon (Tau+/MAP2−) and dendrite (MAP2+) length (* $p<0.01$, t-test; Mean±SEM).

Although KLF4 regulates cell survival in other systems, we detected no differences in survival between KLF4- and control-transfected hippocampal neurons (FIG. 2B). To determine if the growth-suppressive effect was specific either to axons or dendrites, we manually traced Tau+ and MAP2+ neurites (FIG. 2A). Overexpression of KLF4 in embryonic hippocampal neurons significantly decreased the lengths of both axons (Tau+/MAP2−) and dendrites (Tau+/MAP2+) (FIG. 2A, D; FIG. 7). We also observed a reduction in branching (FIG. 8) and in the percentage of neurons that extended neurites (FIG. 2C). Taken together, these findings suggest that KLF4 acts independently of cell survival to suppress axon and dendrite initiation and elongation by hippocampal neurons in vitro.

Figure 3:
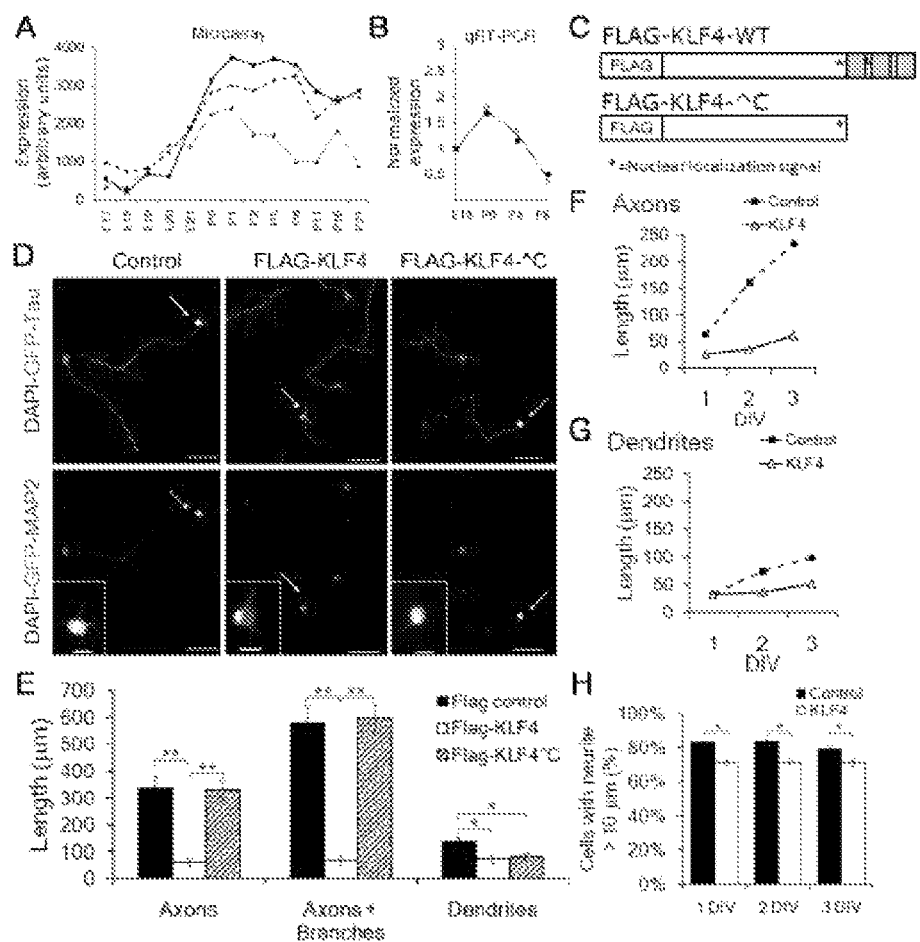
FIG. 3. KLF4 is developmentally regulated in RGCs, and its overexpression decreases axon growth in a zinc-finger-dependent fashion. A-B) KLF4 expression in RGCs increases at birth, as measured in acutely purified rat RGCs by microarray (3 probe sets, A; (19) or in acutely purified mouse RGCs by qRT-PCR (B; fold change from E18). Two biological replicates are plotted with their average in B. C-E) FLAG-KLF4-WT, FLAG-KLF4-ˆC lacking the C-terminal zinc finger DNA binding domain (C), or FLAG or mCHERRY controls were transfected into E20 RGCs. D) RGCs after 2 days were immunostained for FLAG or GFP (green, transfected cells), and Tau or MAP2 (red) as marked (nuclear DAPI is blue). (Scale bar=50 µm, 10 µm inset) E) Hand-tracing revealed that FLAG-KLF4-WT overexpression decreased axon growth; overexpression of FLAG-KLF4-ˆC was similar to controls (** $p<0.001$, * $p<0.02$, unpaired t-test, post-Bonferroni correction; Mean±SEM). F-H) E20 RGCs were transfected with either mCherry-pIRES2-eGFP (control) or KLF4-pIRES2-EGFP and plated for 1, 2 or 3 DIV. Both control— (dashed line) and KLF4— (solid line) transfected neurons elongate axons (F) and dendrites (G) over 3 days, although KLF4-transfected neurons grow less rapidly than controls (* $p<0.003$, unpaired t-tests comparing 1 to 3 DIV for each condition). H) At 1-3DIV, more control-transfected RGCs extended at least 1 neurite >10 µm than KLF4-transfected RGCs (* $p<0.001$, paired t-test; mean±SEM).

We next asked whether KLF4 regulates axon growth of RGCs. KLF4 expression increased postnatally both by microarray analysis Wang et al. (2007), supra; FIG. 3A) and by quantitative reverse transcriptase PCR (qRT-PCR; FIG. 3B) of acutely purified RGCs. We purified RGCs from E20 rats and transfected them with FLAG-tagged KLF4 (Zhang et al. (2006) *Mol Cell Biol* 26, 2055 or a FLAG-only control. Overexpression of KLF4 in embryonic RGCs reduced the percentage of neurons extending neurites (FIG. 3H), reduced neurite branching (FIG. 9), and reduced axon and, less so, dendrite lengths (FIG. 3D-E). The average axon length of KLF4-transfected RGCs continued to increase over three days, but at a slower rate than control transfected neurons, suggesting that KLF4 overexpression decreases elongation rate (FIG. 3F-G; FIG. 10). Furthermore, truncated KLF4 that lacked a C-terminal DNA-binding domain (FIG. 3C) (Zhang et al. (2006) *Mol Cell Biol* 26, 2055) had no effect on axon growth (FIG. 3D-E; FIG. 10). Thus, KLF4 suppresses axon growth in embryonic RGCs, and KLF4's DNA-binding domain is required for its growth-suppressive activity.

We next tested whether knocking out KLF4 in developing RGCs enhances axon growth ability. Because KLF4-null mice die perinatally (Segre et al. (1999) *Nat Genet.* 22, 356), we used a Cre/lox strategy to target KLF4 knockout to RGCs. Floxed-KLF4 mice (Katz et al. (2002) *Development* 129, 2619) were crossed to ROSA-EYFP reporter mice and Thy-1-promoter Cre recombinase mice. Approximately 50% of RGCs purified from Thy-1-cre/ROSA-EYFP mice were EYFP+ (FIG. 11). There was no effect of transgenic Cre expression on RGC neurite growth, neurite initiation or survival in vitro (FIG. 4B, FIG. 12). To examine axon growth from KLF4-deficient RGCs in vitro, RGCs were purified from P12 Thy1-cre$^{+/-}$/KLF4$^{fl/fl}$/ROSA-EYFP$^+$ ("KO") or Thy1-cre$^{-/-}$/KLF4$^{fl/fl}$/ROSA-EYFP$^+$ ("WT") littermate mice and cultured for 3 days (FIG. 4A). No effect of KLF4 KO was seen on survival (FIG. 4B). P12 KLF4 KO RGCs showed a statistically significant increase in neurite initiation compared to controls (FIG. 4C), mirroring our previous finding that overexpression of KLF4 decreases neurite initiation (FIG. 3H). We also observed a significant increase in neurite lengths in KLF4 KO RGCs (FIG. 4D). These data demonstrate that knocking out KLF4 enhances axon growth ability in P12 RGCs in vitro.

We next asked if knocking out KLF4 during development enhances regeneration from adult RGCs in vivo. Thy1-cre$^+$/KLF4$^{fl/fl}$ (KO), Thy1-cre$^+$/KLF4$^{fl/+}$ (Het), or Thy1-cre$^+$/KLF4$^{+/+}$ (WT) littermate mice were subjected to optic nerve crush, and after two weeks we assessed regeneration of RGC axons in the optic nerve. By adulthood, there were no differences in RGC number between KO, Het and WT animals (FIG. 5D). Compared to controls, however, KLF4 KO mice showed an increase in the number of regenerating axons at multiple distances from the injury site (FIG. 5A-B). KLF4 KO did not affect RGC survival after injury (FIG. 5C), showing that this increase in regenerating axons was not secondary to an increased RGC number. Thus, knocking out KLF4 expression during development increases the regenerative potential of adult RGCs.

Although knocking out KLF4 enhanced axon growth and regeneration, the size of the effect led us to speculate that other KLF family members might compensate for the loss of KLF4. The KLF family comprises 17 related transcription factors with homologous DNA-binding domains and divergent activation and repression domains (Kaczynski et al. (2003), supra). KLFs often regulate gene expression interactively, with both cooperative and competitive relationships among family members (Jiang et al. (2008) *Nat Cell Biol* 10, 353; Eaton et al. (2008) *J Biol Chem* 283, 26937; Dang et al. (2002) *Nucleic Acids Res* 30, 2736). Our microarray data suggested that many KLFs are expressed by RGCs (Wang et al. (2007), supra), and that some are developmentally regulated (FIG. 13). We profiled the expression of all 17 KLF family members in developing RGCs by RT-PCR, and detected transcripts for 15 (FIG. 6E). Furthermore, qRT-PCR revealed that KLF6 and KLF7 transcripts decrease more than 10-fold, while KLF9 increases more than 250-fold (FIG. 6A-C). Thus expression of multiple KLFs is regulated in developing RGCs.

Do other KLF family members also regulate neurite growth? Other KLFs can affect neurite branching in response to thyroid hormone (KLF9; Cayrou et al. (2002) *Endocrinology* 143, 2242) or neurite outgrowth in zebrafish retinal explants (KLF6 and -7; (Veldman et al. (2007) *Dev Biol* 312, 596). In RGCs, overexpression of KLF9 significantly decreased growth, similar to KLF4, and KLF6 and -7 increased neurite growth 13% and 23%, respectively (FIG. 6D). We comprehensively surveyed all 17 KLF family members' effects on neurite growth in cortical neurons in vitro, and found that although no KLFs affected cell survival (FIG. 14), eight KLFs including KLF4- and -9 suppressed neurite growth, and KLF6 and -7 again significantly increased neurite growth, 35% and 60%, respectively (FIG. 6E). As with KLF4, effects on neurite growth depended on the DNA-binding domain (FIG. 15). Interestingly, clustering KLFs by sequence similarity revealed an association between functional domains (Kaczynski et al. (2003), supra) and effects on neurite outgrowth (FIG. 6E). For instance, overexpression of the BTEB cluster and the cluster containing KLF4 (FIG. 6E) decreased neurite growth. The TIEG and PVALS/T-containing clusters (FIG. 6E) had no effect on neurite length. KLF6 and KLF7, with 85% homologous activation domains, both increased neurite length (FIG. 6E). To explore coordinate regulation of neurite growth by KLFs, we co-expressed all two-way combinations of KLFs -4, -6, -7 and -9 in cortical neurons. The negative effects of KLF4 on neurite growth were dominant over the otherwise positive effects of KLF6 or -7; the negative effects of KLF9 summed with KLF6 or -7 to no net effect (FIG. 6F), suggesting a complexity to KLF-KLF interactions in regulating neurite growth. Thus, during development, RGCs downregulate at least two growth-enhancing KLFs (KLF6 and -7), and upregulate at least two growth-suppressive KLFs (KLF4 and -9), which may be dominant in their effect over KLF6 and -7.

These findings that the KLF family of transcription factors regulates axon growth in a number of CNS neurons have important implications. First, although KLF4 has been implicated in a wide variety of cellular events including differentiation, cancer progression, and stem cell reprogramming, this function for KLF4 in postmitotic neurons advances our knowledge of the transcriptional regulation of axon regeneration. KLF4 targets relevant for regeneration may include genes selectively expressed in neurons, or important in growth cone function. Second, the clustering of KLF gene function according to domain homology may provide a key for understanding how KLFs cooperate and compete to determine cellular phenotype, whether for axon regeneration or for other systems. Third, the decrease in RGCs' intrinsic axon growth ability parallels changes in expression within the KLF family: postnatal RGCs express higher levels of axon growth-suppressing KLFs and lower levels of axon growth-enhancing KLFs; similar changes can be found in published corticospinal motor neuron data (Arlotta et al. (2005) *Neuron* 45, 207). Thus manipulating multiple KLF genes is likely to be a useful strategy to add to existing approaches to increase the intrinsic regenerative capacity of mature CNS neurons damaged by injury or disease.

Example III

Further Experiments Showing that KLF Family Members Regulate Intrinsic Axon Regeneration Ability 1. KLF4 Overexpression in Hippocampal Neurons Decreases Neurite Growth and Neurite Initiation. The results of this study are shown in FIG. 7. A-D) E18 hippocampal neurons were co-transfected with KLF4 or control plus EGFP, cultured on laminin-coated plates, and immunostained for Tau (neurites) and MAP2 (dendrites). A) There was no difference in survival by nuclear morphology and DAPI intensity between control- and KLF4-transfected neurons (Mean±SD). B) Transfected EGFP+ cells (arrows) were imaged to detect DAPI, EGFP, and either Tau (top) or MAP2 (bottom). KLF4-transfected neurons had shorter axons and dendrites. (Scale bar, 50 µm) C) KLF4 overexpression decreased the percentage of transfected neurons that were able to extend at least 1 neurite >10 µm (N=5; *p<0.01, paired t-test; mean±SEM). D) KLF4 overexpression decreased both axon (Tau+/MAP2−) and dendrite (MAP2+) length (*p<0.01, t-test; mean±SEM).
2. KLF4-Mediated Suppression of Neurite Growth Requires the C-Terminal Zinc Finger Domain. The results of this study are shown in FIG. 8. E18 hippocampal neurons were transfected with either FLAG-KLF4-WT, FLAG-KLF4-^C lacking the C-terminal zinc finger DNA binding domain (A), or mCherry-pIRES2-eGFP as control. B) After 3 DIV, neurons were stained for Tau (neurites) and MAP2 (dendrites) prior to imaging and analysis (Cellomics KSR). Transfected neurons are indicated by arrows. C) Neurite growth was normalized to control transfected neurons (not graphed, equal to 100%). WT KLF4 overexpression significantly decreased neurite growth in both Tau stained and MAP2 stained neurites, while deletion of KLF4's C-terminus led to growth indistinguishable from that of controls (*p<0.01, one representative experiment of 2 shown; mean±SEM).
3. KLF4 Overexpression Decreases Numbers of Both Neurites and Branches in Embryonic Hippocampal Neurons. The results of this study are shown in FIG. 9. E18 hippocampal neurons were electroporated with EGFP and either KLF4 or a pcDNA3 vector control and cultured for 3 days on PDL- and laminin-coated plates in growth media. Following immunostaining, transfected neurons were imaged and hand-traced. There was a decrease in the number of neurites originating from the cell body (A), the number of branches from all neurites (B), and the number of branches normalized to the total neurite length for each transfected neuron (C) after KLF4 overexpression (*p<0.001 for each graph, unpaired t-test; n>50 per condition; mean±SEM).
4. KLF4 Overexpression in Embryonic RGCs Decreases the Numbers of Both Neurites and Branches. The results of this study are shown in FIG. 10. E20 RGCs were purified and transfected using Lipofectamine 2000 with a FLAG control plasmid, FLAG-KLF4, or FLAG-KLF4-^C deletion mutant lacking the C-terminal zinc finger DNA-binding domain. Neurons were plated for 3 days on PDL- and laminin-coated plates in growth media. Following immunostaining, transfected neurons were imaged and hand-traced. KLF4 overexpression decreased the average number of neurites (A), branches (B), and branches normalized to total neurite length of each neuron (C), whereas RGCs overexpressing the truncated Flag-KLF4-^C behaved similarly to controls (p<0.01, unpaired t-test post-Bonferroni; n>25 for each; mean±SEM).

5. RGCs Overexpressing KLF4 Continue to Extend Neurites, but at a Slower Rate. The results of this study are shown in FIG. 11. E20 RGCs were purified and transfected with either KLF4-pIRES2-eGFP or mCherry-pIRES2-eGFP and cultured for 1, 2, or 3 days (DIV) prior to immunostaining for Tau and MAP2. Hand tracing revealed that while KLF4 transfected cells have decreased growth ability, they are still able to grow over a period of days whether looking at axon length (Tau+, MAP2−, A) or dendrite length (Tau+, MAP2+, B) (*p<0.003, unpaired t-tests comparing 1 to 3 DIV for each condition).

6. Half of RGCs Activate Cre in the Thy1-cre$^{+/-}$/Rosa$^{+/-}$ Mice. The results of this study are shown in FIG. 12. Alexa Fluor 594-labeled cholera toxin B was injected into the superior colliculus of P7 Thy1-cre$^{+/-}$/Rosa$^{+/-}$ mice to retrogradely label RGCs (red). Eyes were fixed, sectioned and immunostained to amplify the EYFP signal. A) Retinal cross sections reveal that YFP was expressed in RGCs, as well as in other retinal cells. B) RGCs from P10 Thy1-cre$^{+/-}$/Rosa$^{+/-}$ and Thy1-cre$^{-/-}$/Rosa$^{+/-}$ mice were purified by immunopanning, cultured on PDL- and laminin for 3 days, and immunostained for Tau (neurites) and GFP (to amplify YFP). Images were taken both with a Zeiss microscope and by the Cellomics Kineticscan software to determine intensity of YFP fluorescence. C) Two times the standard deviation of background intensity in Thy1-cre$^{-/-}$/Rosa$^{+/-}$ RGCs yielded a baseline threshold for "YFP+". 46% of RGCs were YFP+, suggesting that this Thy1-cre line is targeting approximately half of immunopanned RGCs.

7. Transgenic Cre Expression does not Affect RGC Neurite Growth. The results of this study are shown in FIG. 13. RGCs from P10 Thy1-cre$^{+/-}$/Rosa$^{+/-}$ and Thy1-cre$^{-/-}$/Rosa$^{+/-}$ mice were purified by immunopanning, cultured on PDL and laminin for 3 days, and immunostained for Tau (neurites) and GFP (to amplify YFP). Cellomics Kineticscan software imaged and traced neurites, and measured YFP intensity. The baseline threshold of YFP intensity indicating cre targeting was determined as in FIG. 12, above. RGCs were grouped either as all RGCs from Thy1-cre− animals (no Cre expression, black bars), YFP− cells from Thy1-cre+ animals (also no Cre, hatched bars), or YFP+ cells from Thy1-cre+ animals (Cre-expressing RGCs, white bars). Neurons with growth <10 μm were not included in the length analysis. Quantification of total neurite length (A) or of percent of RGCs with at least one neurite >10 μm (B) revealed no differences between genotype (A: ANOVA revealed no significant differences between genotype; 1 representative experiment shown, n>2000 for each condition; mean±SEM).

8. KLF4 Knockout does not Affect Survival of RGCs In Vitro. The results of this study are shown in FIG. 14. Purified P12 RGCs were cultured from Thy1-cre$^{-/-}$/KLF4$^{fl/fl}$/Rosa$^+$ (Cre-WT) and Thy1-cre$^{+/-}$/KLF4$^{fl/fl}$/Rosa$^+$ (Cre+ KO) mice. MTT survival assays at 1-3 DIV showed no significant differences in survival between KLF4 KO and WT RGCs (N=3; mean±SEM).

9. KLF4 Knockout During Development does not Affect Adult RGC Number or Survival after Injury. The results of this study are shown in FIG. 15. Two weeks after optic nerve crush of Thy1-cre+/KLF4$^{+/+}$ (WT), Thy1-cre+/KLF4$^{fl/+}$ (Het), and Thy1-cre+/KLF4$^{fl/fl}$ (KO) mice, retinas from both the control eye (uninjured nerve) and injured eye (crushed nerve) were flatmounted and immunostained for βIII tubulin (Tuj1) to label RGCs. Confocal imaging of retinas from knockout animals, normalized to WT, showed no differences in basal RGC number in the contralateral uninjured retinas (A; mean±SEM; n=8 WT, 4 Het, 9 KO) or in RGC survival two weeks after optic nerve crush (B; mean±SEM; n=6 WT, 4 Het, 9 KO).

Figure 4:
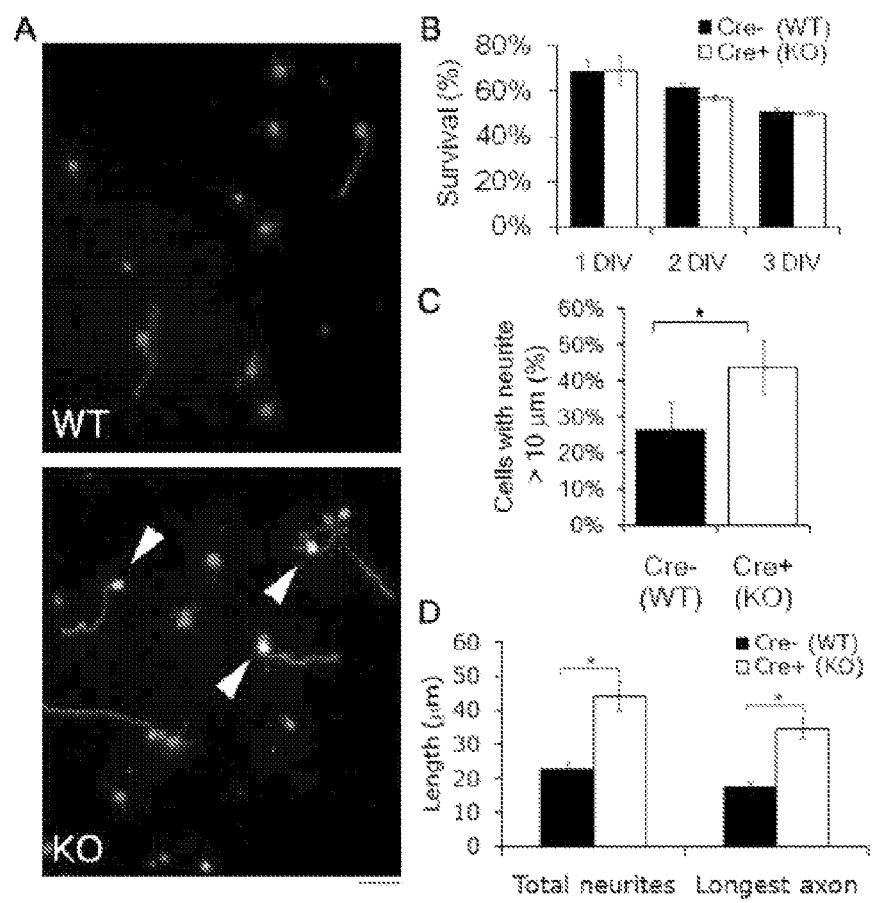
FIG. 4. KLF4 knockout increases RGC neurite growth in vitro. A-D) Purified P12 RGCs were cultured from Thy1-cre[−/−]/KLF4[fl/fl]/Rosa[+] (Cre−WT) and Thy1-cre[+/−]/KLF4[fl/fl]/Rosa[+] (Cre+KO) mice. A) Immunostaining for Tau (red) demonstrated low levels of growth of Cre−WT RGCs (top panel) but increased levels of axon growth of Cre+KO RGCs (bottom panel; Rosa+yellow cells). B) MTT survival assays at 1-3 DIV showed no significant differences in survival between KLF4 KO and WT RGCs (N=3; mean±SEM). C-D) P12 WT or KLF4 KO RGCs were purified and plated for 3 DIV prior to Tau immunostaining and automated tracing. C)

10. Multiple KLFs are Expressed in RGCs and are Developmentally Regulated. The results of this study are shown in FIG. 16. RNA was isolated from acutely purified RGCs from multiple ages and analyzed by microarray analysis on Affymetrix chips (1). 9 of 17 KLFs were probed on these arrays using between 1-3 probes; probes not present in at least 2 samples within one age by the Affymetrix algorithm are marked as "absent" with an asterisk at the end of the line. Occasionally one probe would not detect message while the other probe would, as often happens in microarray datasets. All of these KLFs except for KLF1 were detected in RGCs by RT-PCR (FIG. 4).

11. Overexpression of KLF Transcription Factors does not Affect Cell Survival. The results of this study are shown in FIG. 17. P5 cortical neurons were dissociated, transfected with EGFP or KLFs, and cultured on PDL- and laminin-coated plates in growth media. After 72 hours, the percent of cells that excluded SYTOX orange dye was quantified (Cellomics Kineticscan). Transfection with KLFs did not significantly change neuronal survival (p>0.50, ANOVA with Dunnett's post-test; N=3, n>500; mean±SEM).

12. KLF-Mediated Regulation of Neurite Length in Cortical Neurons Requires the C-Terminal Zinc Finger DNA-Binding Domain. The results of this study are shown in FIG. 18. mCherry control, full length KLF-IRES-mCherry, or zinc finger deletion KLF-^C -IRES-mCherry constructs encoding KLF4, -9, -6, or -7 were transfected into P5 cortical neurons. Neurons were plated for 3 days on laminin and immunostained for beta-III tubulin. Bars represent average total neurite length (Cellomics KSR) of transfected (mCherry+) neurons. Compared to mCherry control-transfected neurons, full length but not truncated KLFs significantly affected neurite lengths. (N=3, n>100; *p<0.05, **p<0.01, ANOVA with post hoc Dunnett's test; mean±SEM).

13. Effect of KLFs in Combinatorial Experiments is Independent of μg of Plasmid Transfected. The results of this study are shown in FIG. 19. 4 μg of control mCherry, 4 μg of full length KLF-IRES-mCherry, or 2 μg of full length KLF-IRES-mCherry plus 2 μg of truncated (non-functional, see FIG. S12) KLF-^C -IRES-mCherry were transfected into P5 cortical neurons. Neurons were plated for 3 days on laminin and immunostained for beta-III tubulin. Bars represent average total neurite length (Cellomics KSR) of transfected (mCherry+) neurons. Neurons transfected with 4 μg and 2 μg of functional KLFs had similar neurite lengths (N=3, n>100; p>0.05, ANOVA with post hoc Dunnett's test; mean±SEM).

From the foregoing and subsequent description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding preferred specific embodiments are to be construed as merely illustrative, and not limiting of the scope of the invention in any way whatsoever. The entire disclosure of all applications, patents, and publications cited above, including U.S. Provisional Application 61/239,873, filed Sep. 4, 2009, and in the figures, are hereby incorporated in their entirety by reference. More particularly, portions of the references are incorporated by reference with respect to the method or finding for which they are cited.

We claim:

1. A method for promoting CNS axon regeneration, comprising
    contacting a neuron with an effective amount of an agent that inhibits the expression or activity of one or more of the members of the Krüppel-like transcription factor (KLF) family that suppress axon growth, and/or
    contacting a neuron with an effective amount of an agent that stimulates the expression or activity in a neuron of one or more of the members of the KLF family that promote axon growth.

2. The method of claim 1, which is carried out in vitro.

3. The method of claim 1, which is carried out in vivo.

4. The method of claim 1, which is carried out in a mammal.

5. The method of claim 1, which is carried out in a human.

6. The method of claim 1, wherein the stimulation of expression is achieved by contacting the neuron with an effective amount of a plasmid which overexpresses a nucleic acid encoding the family member, or by introducing into the neuron the KLF family member or an active fragment thereof.

7. The method of claim 6, wherein the plasmid which overexpresses a nucleic acid encoding the family member is contacted with the neuron by transfection.

8. The method of claim 1, wherein the stimulation of expression is achieved by contacting the neuron with an effective amount of an agent that enhances the effect of a KLF protein that promotes axon growth.

9. The method of claim 8, wherein the agent enhances DNA binding or the recruitment of co-factors.

10. The method of claim 1, wherein the neuron is contacted with an effective amount of an agent that stimulates expression or activity in a neuron of one or more members of the KLF family that promotes axon growth, selected from KLF 6 and 7.

11. The method of claim 1, wherein the neuron is contacted with an effective amount of an agent that inhibits expression or activity in a neuron of one or more members of the KLF family that suppresses axon growth, selected from KLFs 1, 2, 3, 4, 5, 9, 12, 13, 14, 15 and 16.

12. The method of claim 11, further comprising contacting the neuron with an effective amount of an agent that stimulates the expression and/or activity of KLF 6 and/or 7.

13. The method of any one of claim 11, wherein the inhibition of expression is achieved by contacting the neuron with an effective amount of a small interfering RNA (siRNA), microRNA (miRNA), ribozyme, or antisense oligonucleotide that is specific for a nucleic acid encoding the KLF family member.

14. The method of claim 11, wherein the inhibition of activity is achieved by contacting the neuron with an effective amount of a dominant negative form of the KLF family member, a recombinant construct that expresses a dominant negative form of the KLF family member; or an antibody or an aptamer that is specific for the KLF family member.

15. The method of claim 11, which is carried out in vitro.

16. The method of claim 11, which is carried out in vivo.

17. The method of claim 11, which is carried out in a mammal.

18. The method of claim 11, which is carried out in a human.

19. A method for identifying an agent that promotes CNS axon regeneration, comprising contacting neurons with candidate agents, and screening the candidate agents for their ability
    to decrease the expression or activity in a neuron of one or more of the members of the Kruppel-like transcription factor (KLF) family that suppress axon growth, and/or
    to increase the expression or activity in a neuron of one or more of the members of the KLF family that promote axon growth.

20. The method of claim 19, wherein the candidates are screened for their ability to increase expression or activity in a neuron of one or more members of the KLF family that promote axon growth, selected from KLF 6 and 7.

21. The method of claim 19, wherein candidate agents are screened for their ability to decrease the expression or activity in a neuron of one or more of the members of the KLF family that suppress axon growth, selected from KLFs 1, 2, 3, 4, 5, 9, 13, 13, 15 and/or 16.

* * * * *